United States Patent
Lin et al.

(10) Patent No.: US 12,324,560 B2
(45) Date of Patent: Jun. 10, 2025

(54) SYSTEMS AND METHODS FOR DETECTING AN ORIENTATION OF MEDICAL INSTRUMENTS

(71) Applicant: Intuitive Surgical Operations, Inc., Sunnyvale, CA (US)

(72) Inventors: Jue Lin, Evanston, IL (US); Andrew J. Hazelton, San Carlos, CA (US); Changmeng Liu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1075 days.

(21) Appl. No.: 17/258,841

(22) PCT Filed: Jul. 9, 2019

(86) PCT No.: PCT/US2019/040959
§ 371 (c)(1),
(2) Date: Jan. 8, 2021

(87) PCT Pub. No.: WO2020/014198
PCT Pub. Date: Jan. 16, 2020

(65) Prior Publication Data
US 2021/0267440 A1  Sep. 2, 2021

Related U.S. Application Data

(60) Provisional application No. 62/696,126, filed on Jul. 10, 2018.

(51) Int. Cl.
*A61B 1/00* (2006.01)
*A61B 1/018* (2006.01)
(Continued)

(52) U.S. Cl.
CPC .. *A61B 1/000094* (2022.02); *A61B 1/000096* (2022.02); *A61B 1/0005* (2013.01);
(Continued)

(58) Field of Classification Search
CPC . A61B 34/10; A61B 34/25; A61B 2034/2051; A61B 2034/252;
(Continued)

(56) References Cited

U.S. PATENT DOCUMENTS 6,380,732 B1  4/2002  Gilboa
6,389,187 B1  5/2002  Greenaway et al.
(Continued)

FOREIGN PATENT DOCUMENTS

WO  WO-2017030913 A2  2/2017

OTHER PUBLICATIONS

International Preliminary Report on Patentability for Application No. PCT/2019/040959, mailed on Jan. 21, 2021, 09 pages.
(Continued)

*Primary Examiner* — Ajibola A Akinyemi
(74) *Attorney, Agent, or Firm* — Haynes & Boone, LLP.

(57) ABSTRACT

A method for determining a position of a tool being received by a catheter, the method including capturing first images with the tool as the tool is being installed in the catheter. The method also includes generating training images for a deep convolutional neural network (DCNN) by replicating the first images and applying perturbations to the replicated first images. The method also includes training the DCNN by inputting the training images into the DCNN. The method also includes capturing second images with the tool as the tool is being installed in the catheter. The method also includes inputting the second images into the DCNN. The method also includes analyzing the second images with the trained DCNN. The method further includes determining a
(Continued)

configuration of the tool based on the analyzed second images.

22 Claims, 24 Drawing Sheets

(51) Int. Cl.
    *A61B 1/05*         (2006.01)
    *A61B 90/00*      (2016.01)
    *G06T 7/00*        (2017.01)

(52) U.S. Cl.
    CPC ............... *A61B 1/018* (2013.01); *A61B 1/05* (2013.01); *A61B 90/08* (2016.02); *G06T 7/0012* (2013.01); *A61B 2090/0811* (2016.02); *G06T 2207/10024* (2013.01); *G06T 2207/10068* (2013.01); *G06T 2207/20081* (2013.01); *G06T 2207/20084* (2013.01); *G06T 2207/30004* (2013.01)

(58) Field of Classification Search
    CPC ............ A61B 2034/256; A61B 34/30; A61B 2034/254; A61B 90/37; A61B 34/20; A61B 90/361; A61B 2090/365; A61B 2034/105; A61B 5/746; A61B 2017/00119; A61B 2034/2065; A61B 2090/376; A61B 1/05; A61B 1/015; A61B 34/70; A61B 2017/00115; A61B 34/37
    USPC ........................................................ 382/128
    See application file for complete search history.

(56) References Cited

U.S. PATENT DOCUMENTS

| | | |
|---|---|---|
| 7,316,681 B2 | 1/2008 | Madhani et al. |
| 7,772,541 B2 | 8/2010 | Froggatt et al. |
| 8,900,131 B2 | 12/2014 | Chopra et al. |
| 9,259,274 B2 | 2/2016 | Prisco |
| 9,452,276 B2 | 9/2016 | Duindam et al. |
| 2006/0013523 A1 | 1/2006 | Childers et al. |
| 2006/0149129 A1* | 7/2006 | Watts ............... A61M 25/0152 600/113 |
| 2011/0263935 A1 | 10/2011 | Qiu |
| 2015/0087899 A1 | 3/2015 | Kung et al. |
| 2016/0081530 A1 | 3/2016 | Imaizumi et al. |
| 2016/0379352 A1 | 12/2016 | Zhang et al. |
| 2017/0020395 A1* | 1/2017 | Malchano ............. A61B 5/349 |
| 2017/0061625 A1 | 3/2017 | Estrada et al. |
| 2017/0143191 A1 | 5/2017 | Haraguchi et al. |
| 2021/0217167 A1* | 7/2021 | Lee ....................... G06N 3/045 |
| 2022/0142713 A1* | 5/2022 | Oren ..................... A61B 5/287 |

OTHER PUBLICATIONS

International Search Report and Written Opinion for Application No. PCT/US2019/040959, mailed on Nov. 22, 2019, 17 pages (ISRG11490/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

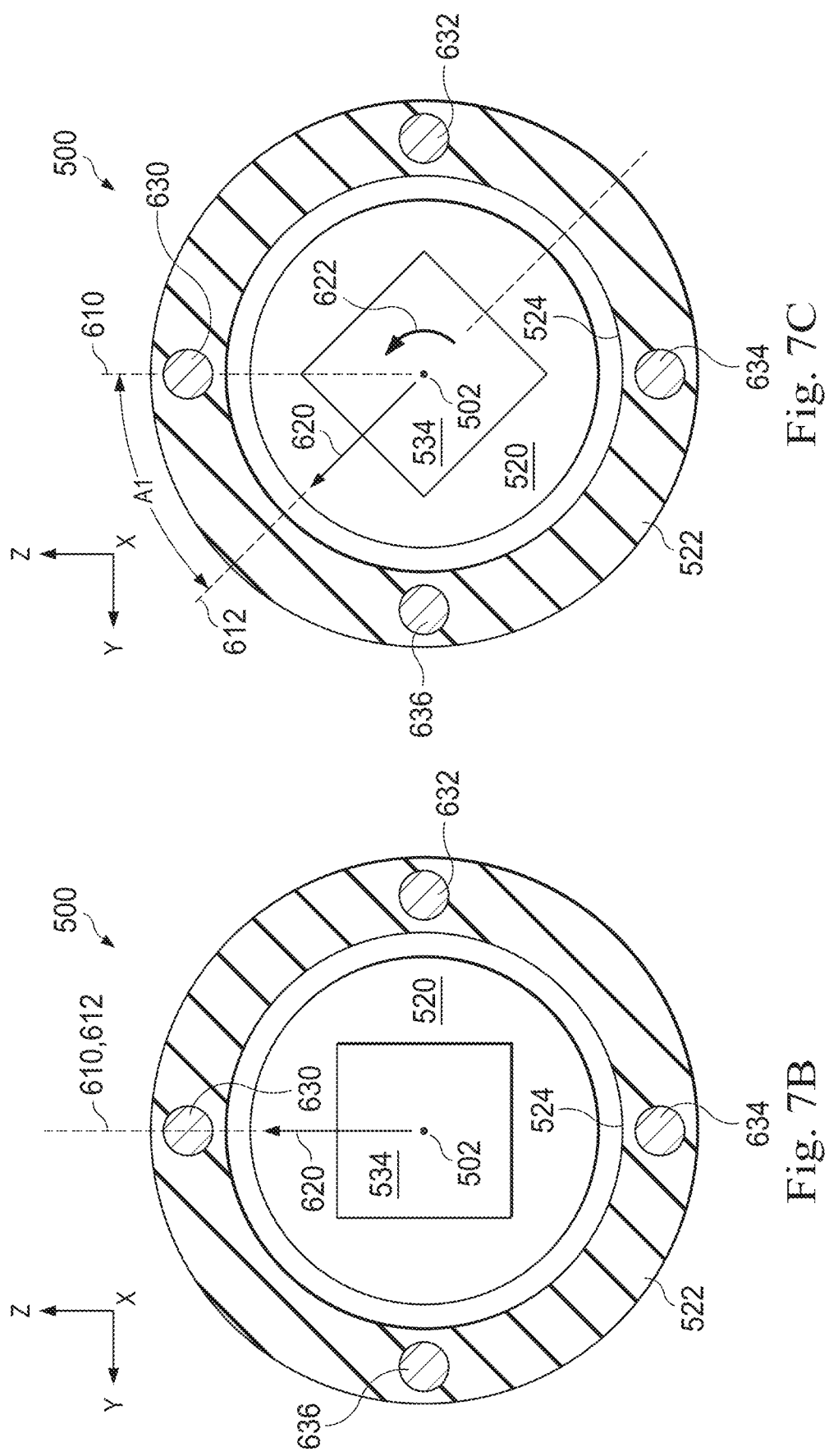

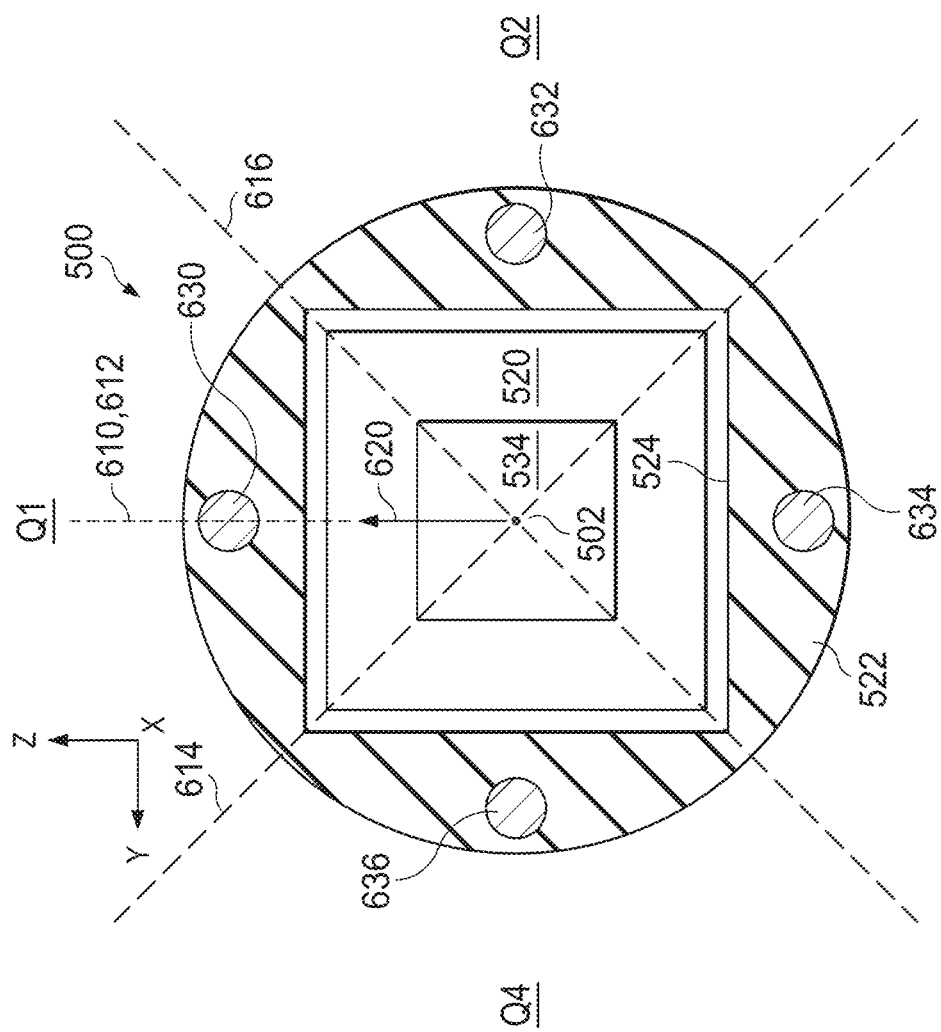

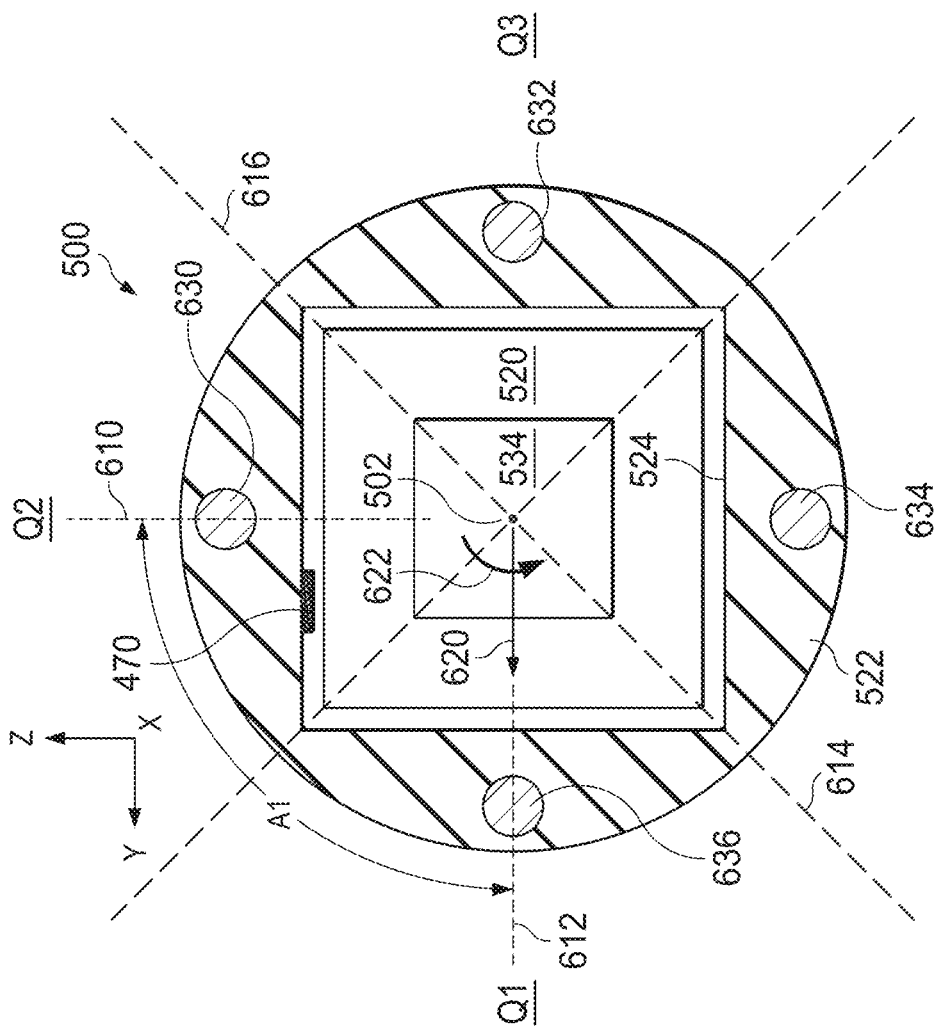

SYSTEMS AND METHODS FOR DETECTING AN ORIENTATION OF MEDICAL INSTRUMENTS

CROSS-REFERENCE TO RELATED APPLICATIONS

This application is the U.S. national phase of International Application No. PCT/US2019/040959, filed Jul. 9, 2019, which designated the U.S. and claims priority to and the benefit of U.S. Provisional Application No. 62/696,126 filed Jul. 10, 2018, both of which are incorporated by reference herein in their entireties.

TECHNICAL FIELD

The present disclosure is directed to systems and methods for determining a configuration of a tool relative to a catheter.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert minimally invasive medical instruments (including surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device.

Accordingly, systems and methods for improved control of the elongate device during minimally invasive medical techniques are needed.

SUMMARY

Some embodiments of the invention are best summarized by the claims that follow the description.

Consistent with some embodiments, a method for determining a position of a tool being received by a catheter is provided. The method may include capturing first images with the tool as the tool is being installed in the catheter. The method may further include generating training images for a deep convolutional neural network (DCNN) by replicating the first images and applying perturbations to the replicated first images. The method may further include training the DCNN by inputting the training images into the DCNN. The method may further include capturing second images with the tool as the tool is being installed in the catheter. The method may further include inputting the second images into the DCNN. The method may further include analyzing the second images with the trained DCNN. The method may further include determining a configuration of the tool based on the analyzed second images.

Consistent with some embodiments, a system is provided. The system may include a catheter sized to receive an imaging tool. The system may further include a processor configured to receive first images from the tool as the tool is being inserted in the catheter. The processor may further be configured to generate training images for a deep convolutional neural network (DCNN) by replicating the first images and applying perturbations to the replicated first images. The processor may further be configured to train the DCNN by inputting the training images into the DCNN. The processor may further be configured to receive second images from the tool as the tool is being inserted in the catheter. The processor may further be configured to input the second images into the DCNN. The processor may further be configured to analyze the second images with the trained DCNN. The processor may further be configured to determine a configuration of the tool based on the analyzed second images.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 7B is a simplified cross-sectional end view of the distal portion of the catheter assembly of FIG. 7A with a tool rotationally aligned with a catheter according to some embodiments.

FIG. 7C is a simplified cross-sectional end view of the distal portion of the catheter assembly of FIG. 7A with a tool rotationally offset from a catheter according to some embodiments.

FIG. 8D is a simplified cross-sectional end view of the distal portion of the catheter assembly of FIG. 8A with a tool rotationally aligned with a catheter according to some embodiments.

FIG. 8E is a simplified cross-sectional end view of the distal portion of the catheter assembly of FIG. 8A with a tool rotationally offset from a catheter according to some embodiments.

Figure 1:
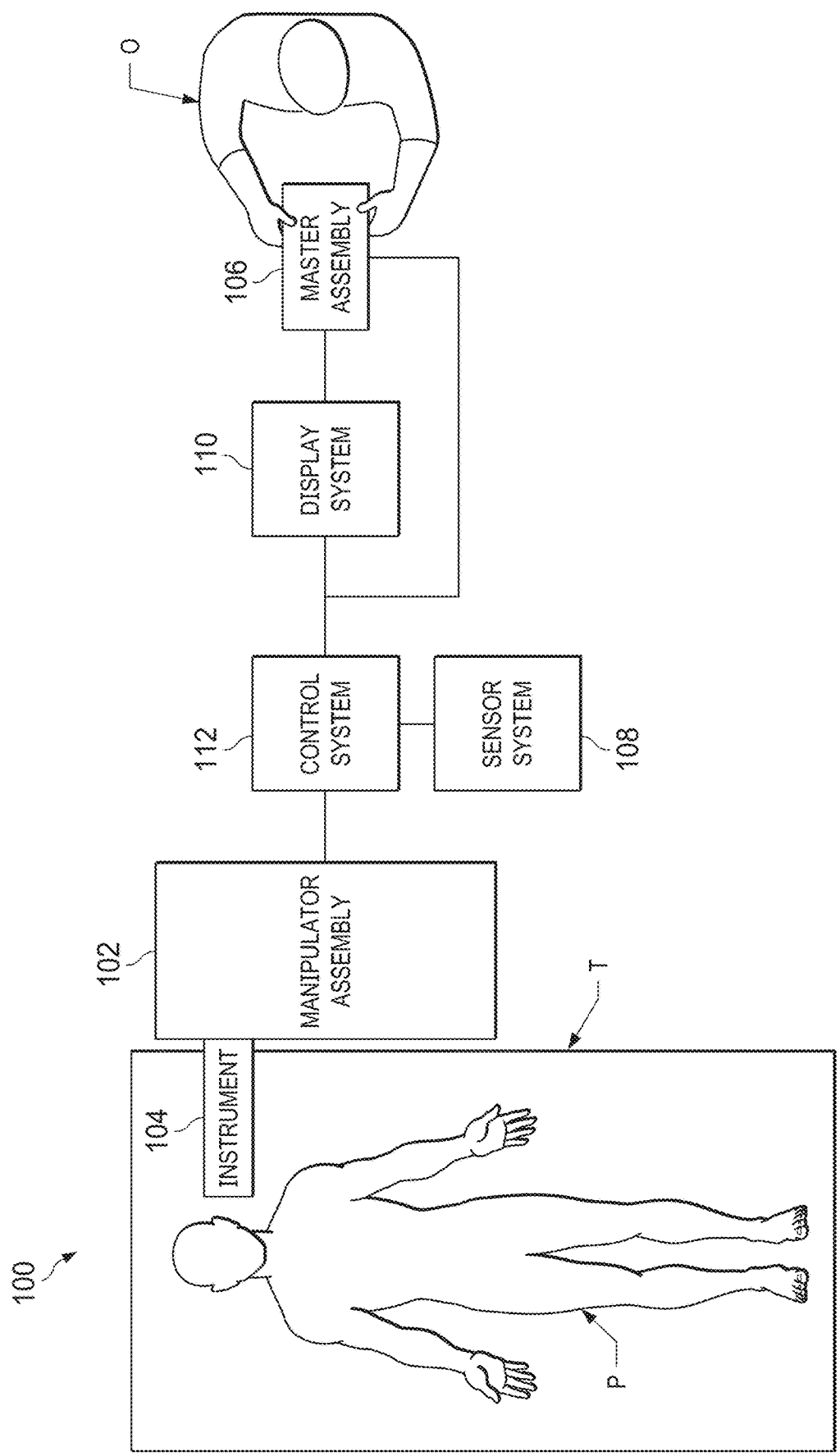
FIG. 1 is a simplified schematic diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperated medical systems.

As shown in FIG. 1, medical system 100 generally includes a manipulator assembly 102 for operating a medical instrument 104 in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is usually located in the same room as operating table T, such as at the side of a surgical table on which patient P is located. However, it should be understood that the operator O can be located in a different room or a completely different building from patient P. Master assembly 106 generally includes one or more control devices for controlling manipulator assembly 102. The control devices may include any number of a variety of input devices, such as joysticks, trackballs, data gloves, trigger-guns, hand-operated controllers, voice recognition devices, body motion or presence sensors, and/or the like. To provide the operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g. one more links that may be controlled in response to commands from the control system), and a manipulator. Manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable portion of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of image-guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory (not shown) and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the control system 112 may include two or more data processing circuits distributed throughout the teleoperated medical system 100 to perform distributed data processing. For example, one portion of the data processing performed by the distributed control system 112 can optionally be performed on or adjacent to manipulator assembly 102, another portion of the data processing can optionally be performed at master assembly 106, and other portions of the data processing can optionally be performed at other data processing circuits. The at least one computer processor or the two or more data processing circuits of control system 112 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperated medical systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104. Medical instrument 104 may extend into an internal surgical site within the body of patient P via one or more openings in the body of patient P. Any suitable conventional and/or specialized actuators may be used. In some examples, the one or more actuators may be separate from, or integrated with, manipulator assembly 102. In some embodiments, the one or more actuators and manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The sensor system 108 may implement one or more electromagnetic (EM) sensor, fiber optic sensors, and/or other sensors to register and display a medical instrument together with preoperatively recorded surgical images. For example, U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such sensor system. Teleoperated medical system 100 may further include optional operations and support systems (not shown) such as illumination systems, steering control systems, irrigation systems, and/or suction systems. In some embodiments, teleoperated medical system 100 may include more than one manipulator assembly and/or more than one master assembly. The total number of teleoperational manipulator assemblies included in the teleoperated medical system will depend on a number of factors including the surgical procedure and the space constraints within the operating room. When implemented as multiple units, master assembly 106 may be collocated or positioned in separate locations. Multiple master assemblies allow more than one operator to control one or more teleoperational manipulator assemblies in various combinations.

Figures 2A, 2B:
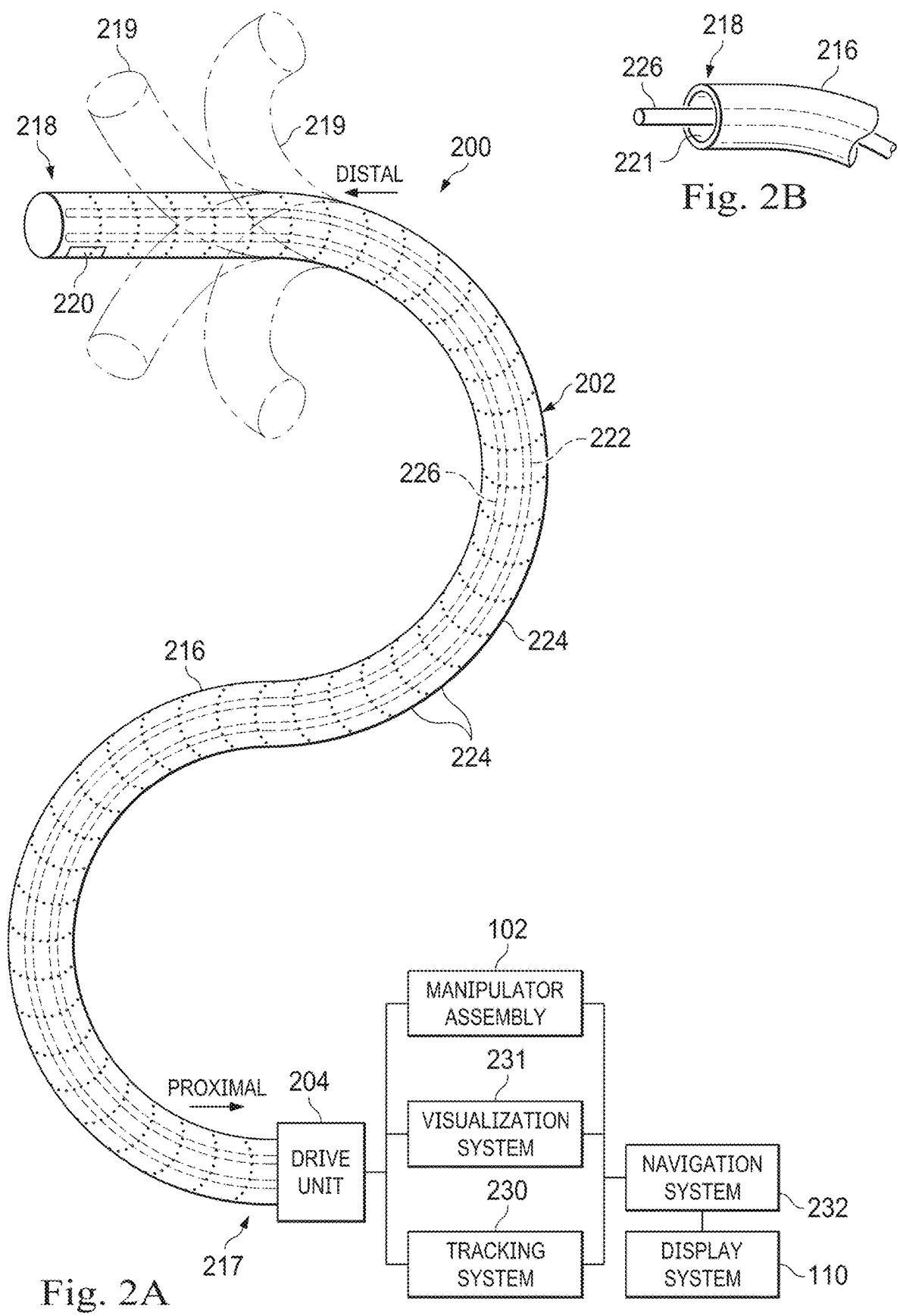
FIG. 2A is a simplified partial-schematic diagram of a medical instrument system according to some embodiments.
FIG. 2B is a simplified diagram of a medical instrument with an extended medical tool according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally, medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end 218 (which may be a tip portion in some embodiments). In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or one or more segments 224 along flexible body 216 using one or more sensors and/or imaging devices as described in further detail below. The entire length of flexible body 216, between distal end 218 and proximal end 217, may be effectively divided into segments 224. Tracking system 230 may optionally be implemented as hardware, firmware, software or a combination thereof which interact with or are otherwise executed by one or more computer processors, which may include the at least one processor or the two or more data processing circuits of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 m. In other embodiments, the dimensions of the optical fiber may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties.

Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over a given interval of time. In some embodiments, tracking system 230 may optionally and/or additionally track distal end 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical tool 226. FIG. 2B is a simplified diagram of flexible body 216 with medical tool 226 extended according to some embodiments. In some embodiments, medical tool 226 may be used for procedures such as surgery, biopsy, ablation, illumination, irrigation, or suction. Medical tool 226 can be deployed through channel 221 of flexible body 216 and used at a target location within the anatomy. Medical tool 226 may include, for example, image capture probes, biopsy instruments, laser ablation fibers, and/or other surgical, diagnostic, or therapeutic tools. Medical tools may include a single working member such as a scalpel, a blunt blade, an optical fiber, an electrode, and/or the like. Other medical tools may include, for example, forceps, graspers, scissors, clip appliers, and/or the like. Other medical tools may further include electrically activated tools such as electrosurgical electrodes, transducers, sensors, and/or the like. In various embodiments, medical tool 226 is a biopsy instrument, which may be used to remove sample tissue or a sampling of cells from a target anatomic location.

Medical tool 226 may be used with an image capture probe also within flexible body 216. In various embodiments, medical tool 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical tool 226 may itself be the image capture probe. Medical tool 226 may be advanced from the opening of channel 221 to perform the procedure and then retracted back into the channel when the procedure is complete. Medical tool 226 may be removed from proximal end 217 of flexible body 216 or from another optional instrument port (not shown) along flexible body 216.

Medical tool 226 may additionally house cables, linkages, or other actuation controls (not shown) that extend between its proximal and distal ends to controllably the bend distal end of medical tool 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician or other operator with real-time position information. In some examples, the real-time position information may be displayed on display system 110 of FIG. 1 for use in the control of medical instrument system 200. In some examples, control system 112 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, manipulator assembly 102 of FIG. 1 may be replaced by direct operator control. In some examples, the direct operator control may include various handles and operator interfaces for hand-held operation of the instrument.

Figure 3A:
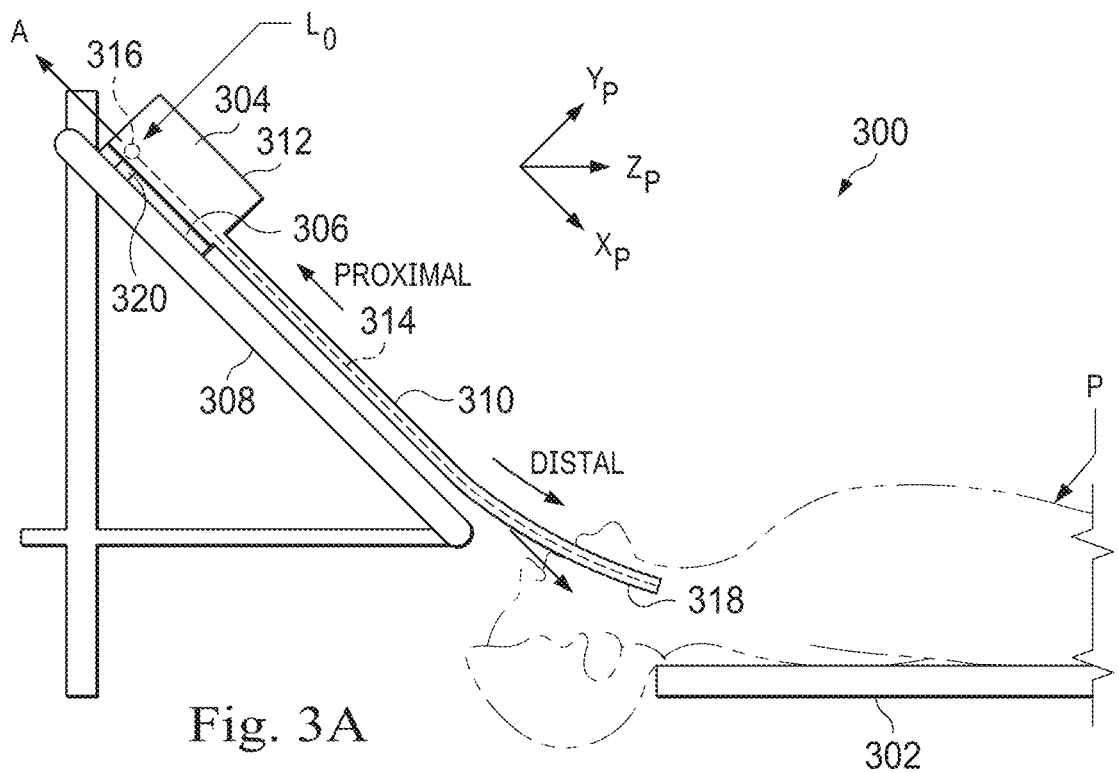
FIGS. 3A and 3B are simplified diagrammatic side views of a patient coordinate space including a medical instrument mounted on an insertion assembly according to some embodiments.
Figure 3B:
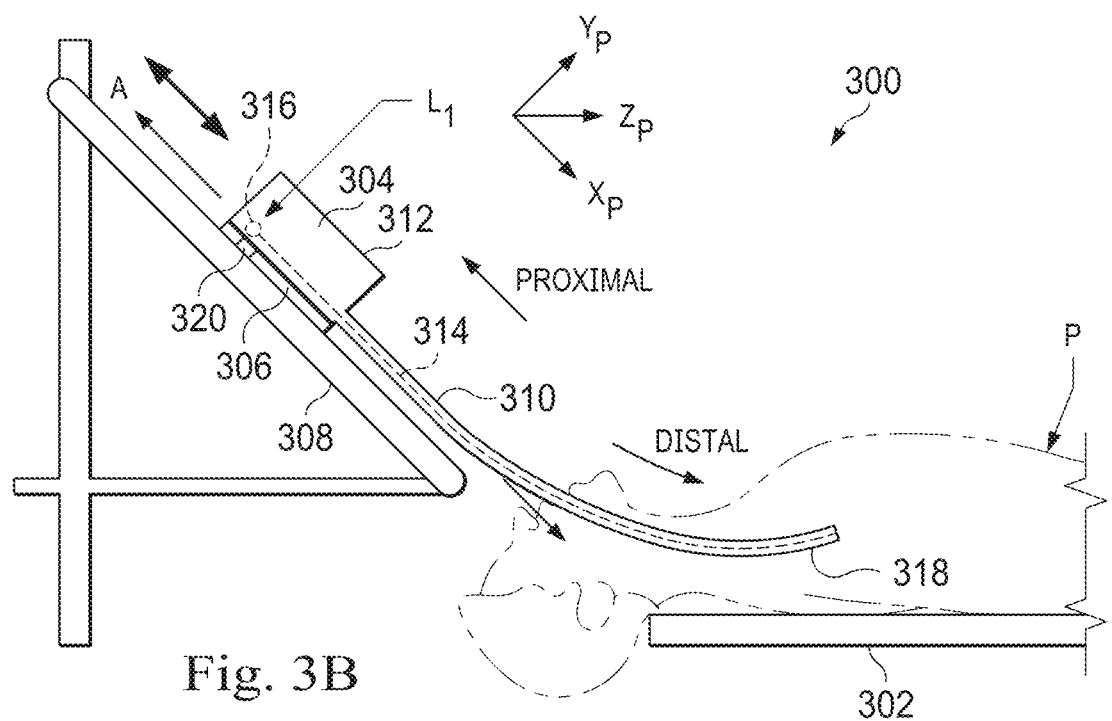

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 (e.g. a medical instrument) can be coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308, a component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_x$ may further be used as an indicator of the distance or insertion depth to which distal end 318 of elongate device 310 is inserted into the passageways of the anatomy of patient P.

In some embodiments, a tool (e.g., medical tool 226) may be installed in a catheter, and the tool can include an imaging sensor for collecting images, for example, during a procedure. If the tool, inserted through the catheter lumen, is not rigidly coupled to the catheter, the tool can rotate relative to the catheter.

A real-time control system based on vision feedback can be used to measure a rotational offset of the tool relative to the catheter. Images captured during a procedure can be adjusted to remove the rotational offset so the resulting adjusted images create the appearance that the tool is rotationally aligned with the catheter.

The vision feedback may be in the form of images captured by an imaging sensor at a distal portion of a tool with the images processed to highlight feature(s) on a catheter or fixed relative to the catheter that can be used to determine the angular orientation of the tool within the catheter. However, the captured images, and thus the highlighted features can be of various qualities with some images providing clearer views of the features while others may provide a poor quality image making it somewhat uncertain as to what the image contains. One way to increase the confidence in the determined angular orientations is to collect many more images and average or otherwise combine statistical information for each image and use confidence weighting to indicate which of a plurality of possible angular orientations determined from the various images may be the most accurate.

In this disclosure, an artificial neural network such as a convolution deep neural network, which may be part of the control system 112, may be used to process the captured images to provide possible angular orientations for the tool and also a location of the tool (e.g., outside the catheter, inside the catheter, inside a patient's anatomy). The neural network can be trained to predict the angular orientations based on the captured image that the neural network processes. This disclosure describes an approach to training a neural network and using the neural network to determine the location of the tool and an angular orientation of the tool when it is inside a catheter.

Figure 4:
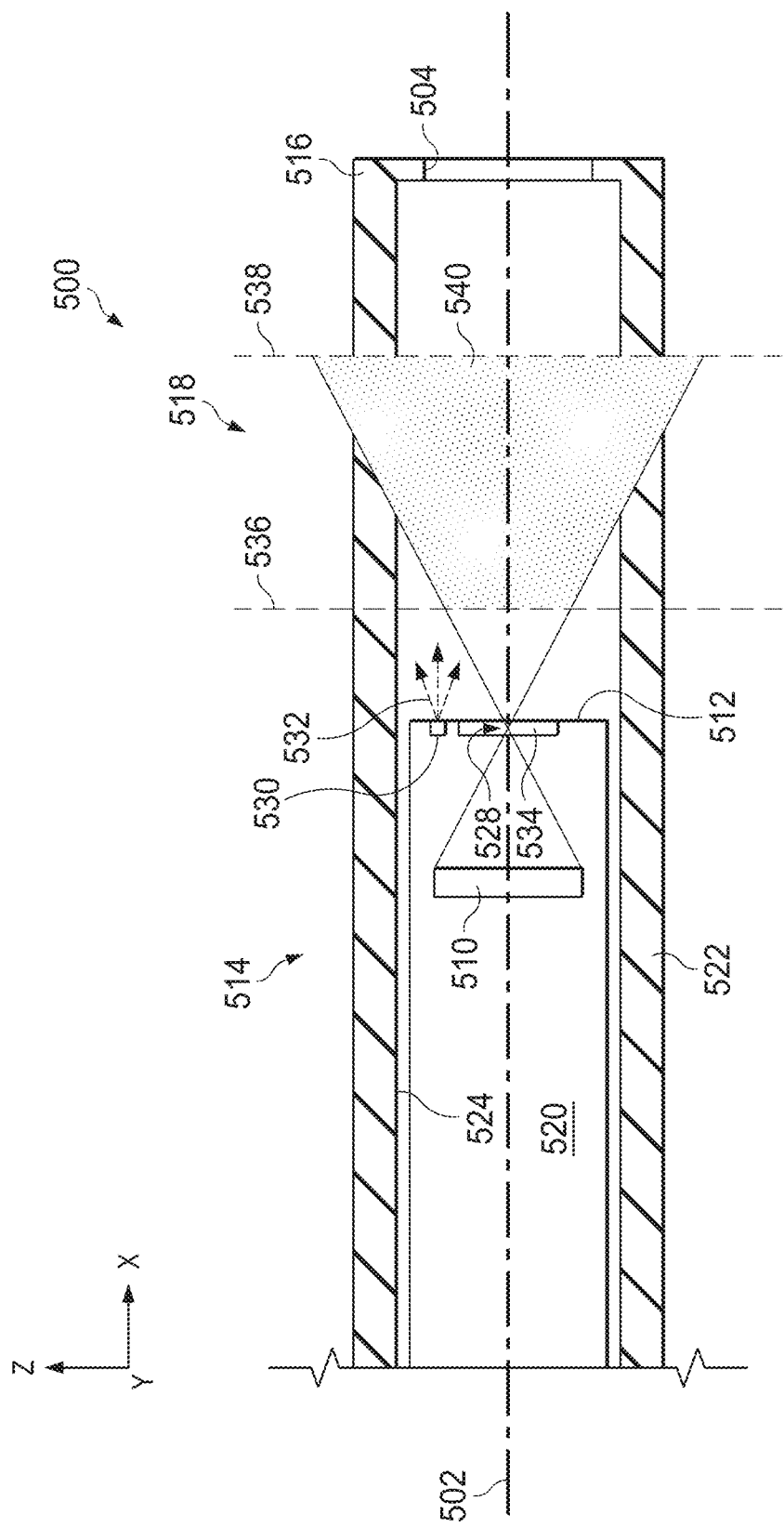
FIG. 4 is a simplified partial cross-sectional view of a distal portion of a catheter assembly according to some embodiments.

Referring to FIG. 4, a simplified partial cross-sectional view of a distal portion 518 of a catheter assembly 500 is provided. An X-Y-Z coordinate reference is given for purposes of discussion and does not limit the disclosure. As shown in FIG. 4, the X-axis can be parallel to the central axis 502, with the Y- and Z-axes being perpendicular to the central axis 502. A tool 520 is partially installed in a lumen 524 of a catheter 522 and spaced away from the distal end 516 of the catheter 522. An imaging sensor 510 is positioned in a distal portion 514 of the tool 520 and has a viewable region 540 that extends from a distal end 512. A lens 534 can be positioned at the distal end 512 and have an optical center of the lens 528. The lens 534 can establish the viewable region 540 in front of the imaging sensor 510, where the near point 536 and the far point 538 are extreme ends of the viewable region 540. It should be understood that the viewable region 540 is not necessarily to scale and that the far point 538 of the viewable region 540 can extend much further than indicated by the illustration in FIG. 4. Also, the near point 536 can be closer or farther away than shown in FIG. 4. The imaging sensor 510 may capture both low frequency light (such as light within a human visual spectrum) and high frequency light (such as infrared light). An optical source 530 can be disposed at the distal end 512 of the tool 520 and/or disposed at the distal end 516 of the catheter 522. The optical source 530 can illuminate the lumen 524 via optical signals 532 as the tool 520 is being inserted into the catheter 522 and illuminate objects outside of the lumen 524 when the tool 520 is fully inserted (i.e. inserted to a position in the catheter 522 that allows full functionality of the tool 520).

Figure 5:
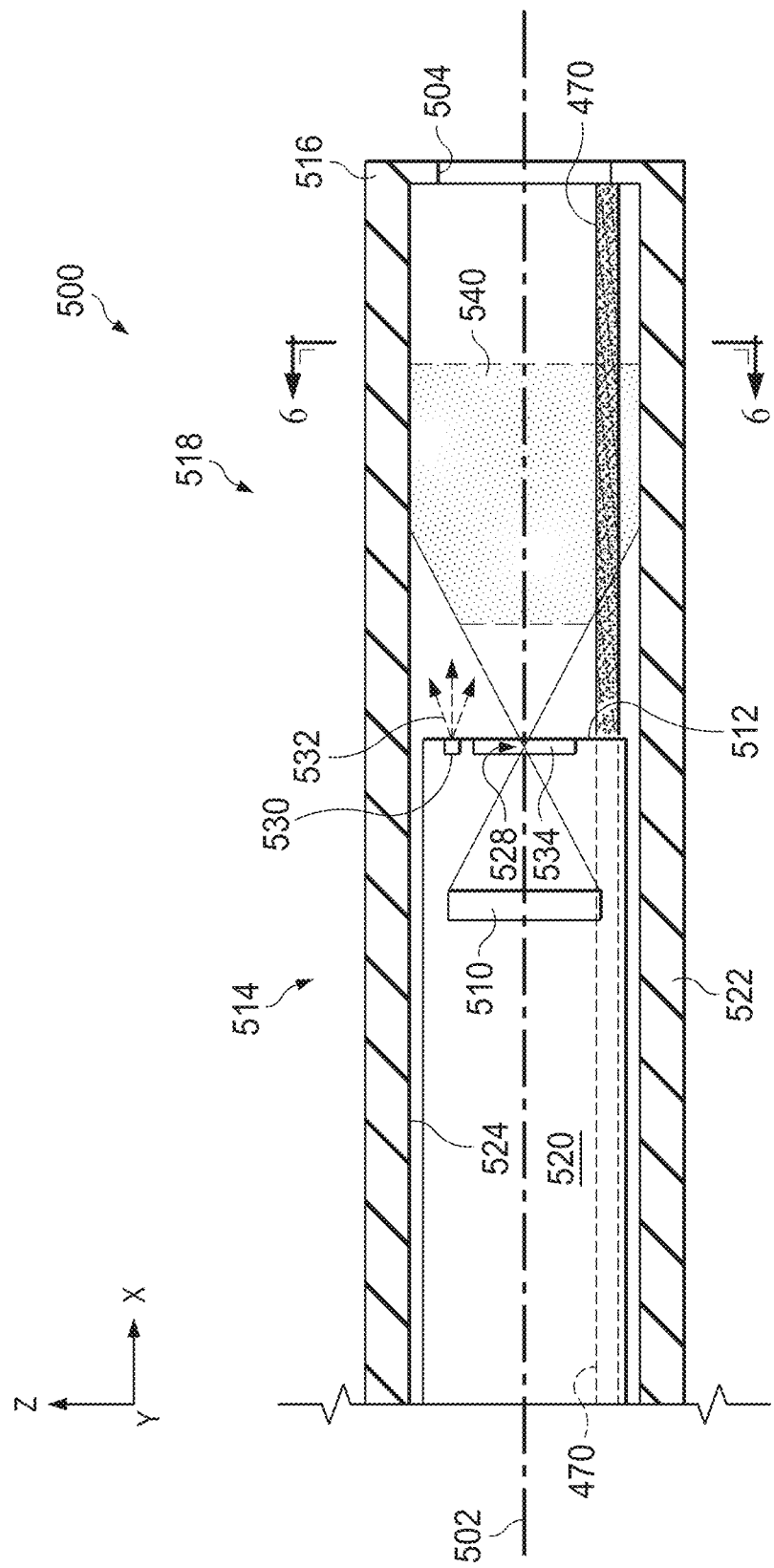
FIG. 5 is a simplified partial cross-sectional view of a distal portion of a catheter assembly with a longitudinal marking according to some embodiments.

Referring now to FIG. 5, a simplified partial cross-sectional view of the distal portion 518 of the catheter assembly 500 is shown. In this embodiment a viewable feature may be a longitudinal marking 470 (e.g. a marking extending parallel to the central axis 502) formed on an interior surface of the lumen 524. The longitudinal marking 470 may be a contrasting feature to the rest of the interior surface of the lumen, e.g. a different color, different texture, etc. The rest of the surface can be referred to as a background layer of the lumen. The marking 470 provides sufficient contrast between the background layer (e.g. a background color) that the marking can be seen in images captured by the image sensor 510 within the catheter 522. The viewable region 540 gives the imaging sensor 510 a 360 degree view of the interior surface of the lumen 524 ahead of the distal end 512 of the tool 520. The longitudinal marking 470 is formed at a pre-determined angular position in the lumen 524. Therefore, the angular relationship between the marking 470 and the catheter 522 is fixed. When the imaging sensor 510 captures an image within the lumen 524, the longitudinal marking 470 will appear in the images at an angular position in the 360 degree view of the image sensor 510. The longitudinal marking 470 can be any feature that is visible on the inside surface of the lumen 524 and is distinguishable from the rest of the inner surface of the lumen 524. Also, the longitudinal marking 470 can occupy a small circumferential distance of the inner surface when compared to the full circumferential distance around the inner surface. Therefore, the longitudinal marking can be referred to as a longitudinal stripe that extends along at least a portion of the lumen's interior surface.

Figure 6:
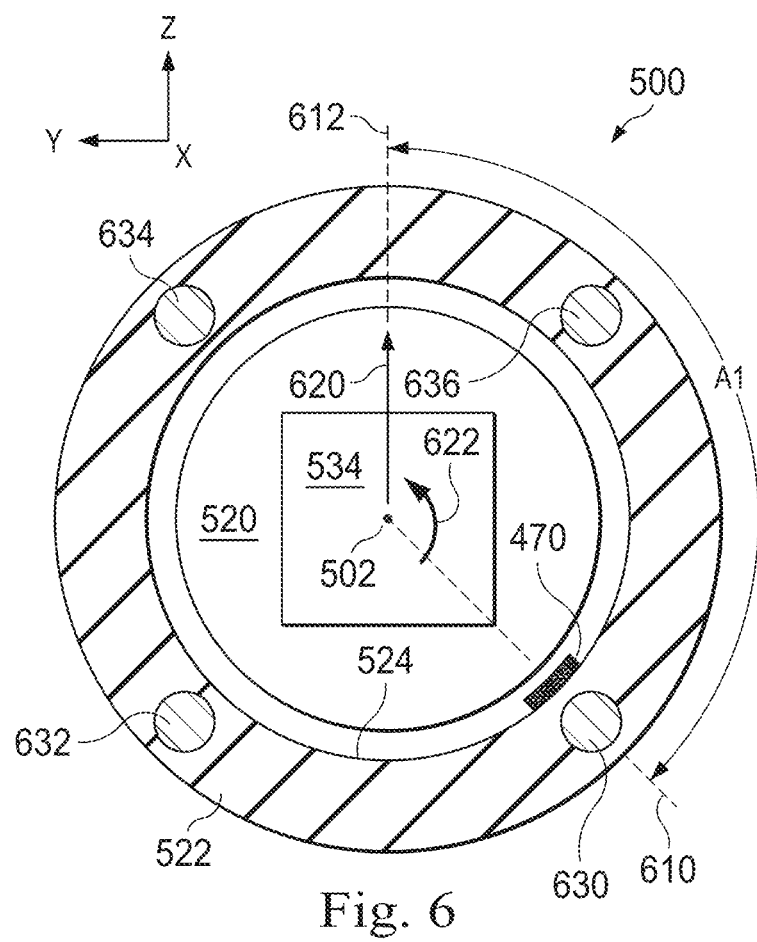
FIG. 6 is a simplified cross-sectional end view of the distal portion of the catheter assembly of FIG. 5 according to some embodiments

FIG. 6 illustrates a simplified cross-sectional end view at the distal portion 518 of the catheter assembly 500 of FIG. 5. As indicated by a rotational arrow 622 (which may indicate angular rotation in some embodiments), the tool 520 may become rotated about the central axis 502 relative to the catheter 522 and the catheter steering cables 630-636. The rotation may occur, for example, during installation of the tool 520 and/or due to other factors, such as manufacturing tolerances. An angular position 610 indicates the 0 (zero) degree angular position of the catheter 522 relative to the catheter and the angular position 612 indicates the 0 (zero) degree angular position of the tool 520 relative to the tool. The angular distance between the angular position 610 of the catheter 522 and the angular position 612 of the tool 520 is referred herein as a rotational offset A1. The resulting rotational offset A1 (or angular offset) can be seen in captured images within the lumen 524 by the angular position of the longitudinal marking 470 within the 360 degree view of the imaging sensor 510. It should be understood that the rotation 622 can be in the opposite direction (i.e. clockwise) to arrive at the angular position 612 shown in FIG. 6. The arrow 620 indicates the angular position of the top-middle of the imaging sensor, and therefore indicates the top-middle of images captured by the image sensor 510.

Figure 7A:
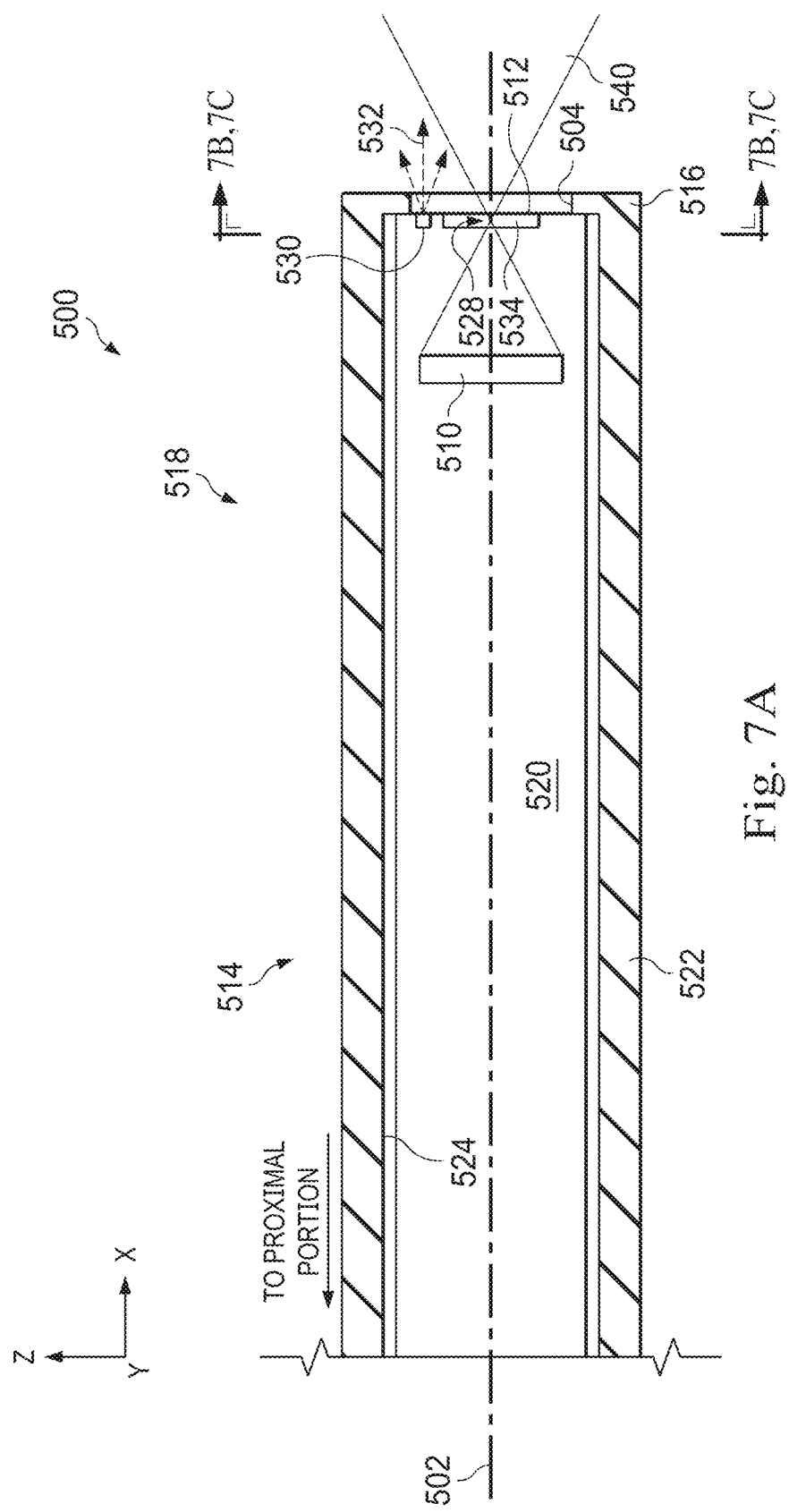
FIG. 7A is a simplified partial cross-sectional view of a distal portion of a catheter assembly according to some embodiments.

Referring now to FIG. 7A, a simplified partial cross-sectional view of a distal portion 518 of the catheter assembly 500 is shown. This catheter assembly 500 is similar to the catheter assembly in FIG. 5, except that the distal end 512 of the tool 520 engages the distal end 516 of the catheter 522. The optical source 530 provides illumination light 532 for objects viewable through the opening 504.

Referring now to FIGS. 7B-7C, a simplified cross-sectional view of the distal portion 518 of the catheter assembly 500 of FIG. 7A is shown. In this example, the tool 520 and the catheter 522 have circular cross-sections as shown by the FIGS. 7B-7C. The cross-sectional views are viewed in the direction toward the viewable region 540 (i.e. toward the distal end 516 of the catheter 522). As briefly mentioned above, cables (such as cables 630, 632, 634, 636) may be used to provide independent "up-down" steering to control a pitch of distal end 516 of the catheter 522 and "left-right" steering to control a yaw of distal end 516. Steering the distal end 516 of the catheter 522 "up-down" and "left-right" are movements that are relative to the orientation of the cables 630, 632, 634, 636. If the catheter 522 is rotationally aligned with the tool 520, then the "up-down" and "left-right" movements are also relative to the orientation of the tool 520. Therefore, images captured by the tool 520 provide a rotationally correct representation of the orientation of the catheter 522 when the tool 520 and catheter 522 are rotationally aligned. If captured images received from the tool 520 show the distal end 516 should be steered "upward" (relative to the captured images), then cables 630 and 634 can be used to achieve an upward steering articulation of the distal end 516.

However, if the tool 520 is not rotationally aligned, then the images captured by the tool 520 provide a user with an incorrect rotational representation of the catheter 522. In this case, if the captured images received from the tool 520 indicate the distal end 516 should be steered "upward," manipulating only cables 630 and 634 will not achieve the desired steering direction. To move the distal end 516 in the direction of the arrow 620 (which would be "upward" relative to the captured images), all four cables 630, 632, 634, 636 may need to be manipulated. The arrow 620 indicates the top-middle position of the imaging sensor 510 relative to the central axis 502. To allow a user to steer the distal end 516 in a desired direction, the rotational offset between the tool 520 and catheter 522 can be determined and the manipulations of the cables 630, 632, 634, 636 can be adjusted to correctly steer the distal end 516.

FIG. 7B shows the tool 520 rotationally aligned with the catheter 522. The angular position 612 of the tool 520 is aligned with the angular position 610 of the catheter 522. FIG. 7C shows the tool 520 offset from the catheter 522 by a rotational offset A1. The angular rotation 622 has rotated the tool 520 relative to the catheter 522 by a rotational offset A1. Using images captured by the imaging sensor 510, the rotational offset A1 can be determined and steering mechanisms of the catheter 522 (such as the cables 630, 632, 634, 636) can be operated to compensate for the rotational offset A1.

Figure 8A:
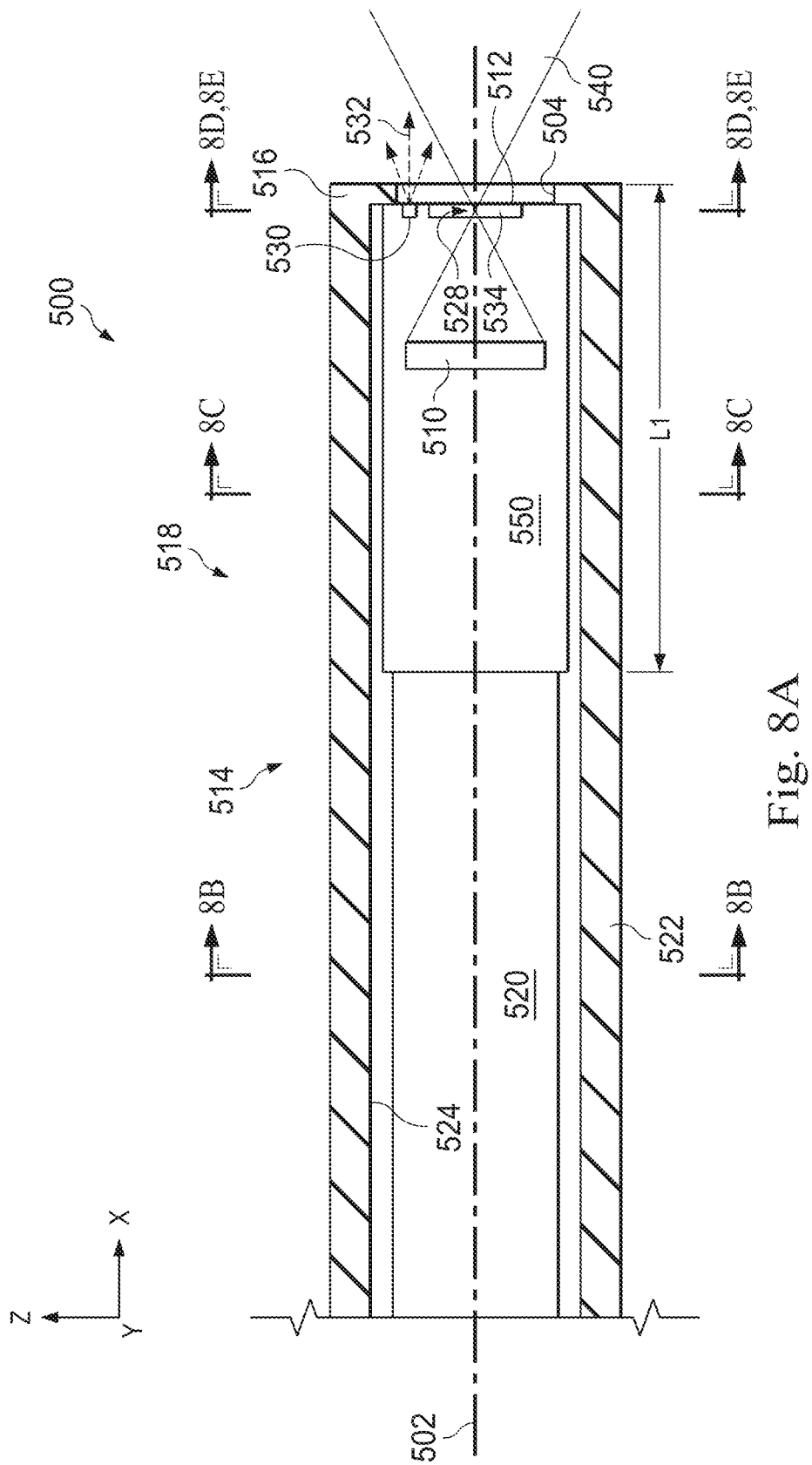
FIG. 8A is a simplified partial cross-sectional view of a distal portion of a catheter assembly with distal portion of a tool having a square cross-section according to some embodiments.

Referring now to FIG. 8A, a simplified partial cross-sectional view of the distal portion 518 of the catheter assembly 500 is shown. This catheter assembly 500 is similar to the catheter assembly in FIG. 7A, except that a distal portion 550 of the tool 520 has a square cross-section where the rest of the tool 520 has a circular cross-section. The square cross-section of the distal portion 550 matches a square cross-section of the lumen 524 of the catheter 522. The square cross-sections of the distal portion 550 and the catheter 522 do not require an additional key system to prevent rotation of the tool 520 relative to the catheter 522, when the distal portion 550 is inserted into the matching square cross-section of the lumen 524. Some rotation may be allowed due to clearances between the tool 520 and the catheter 522, but this is minor, and even this minor relative rotation can be compensated for by using the principles of this disclosure.

Figure 8C:
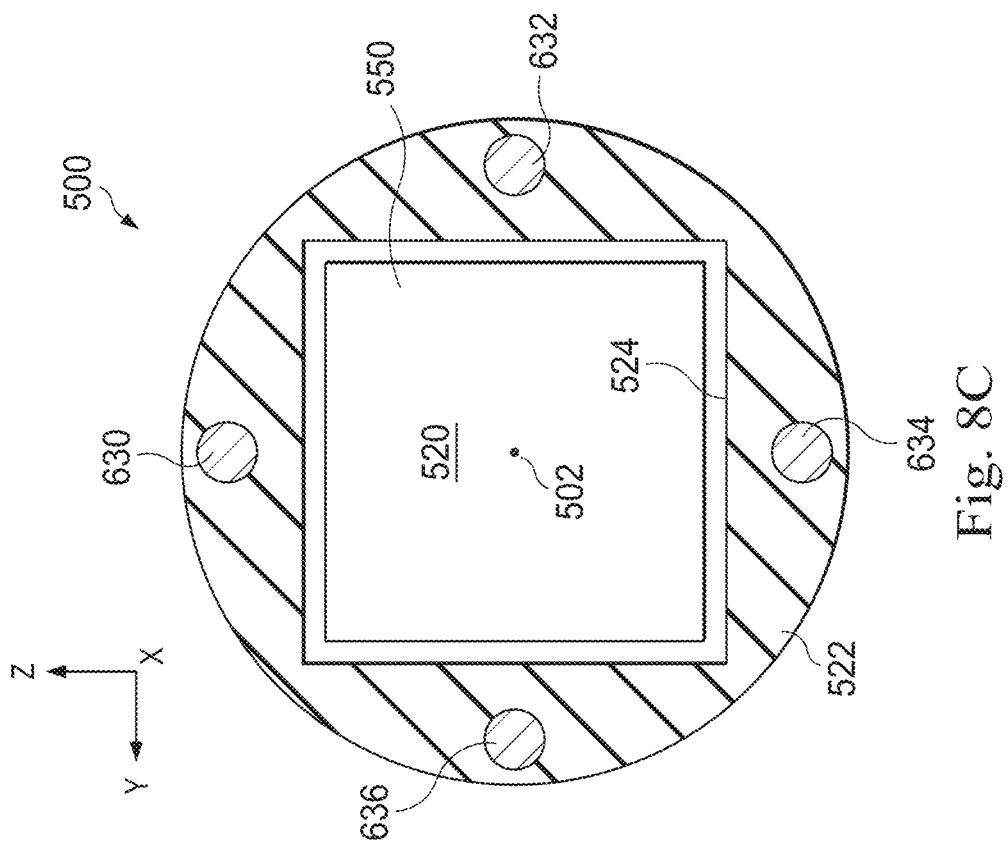
FIG. 8C is another simplified cross-sectional end view of the catheter assembly of FIG. 8A according to some embodiments.
Figure 8B:
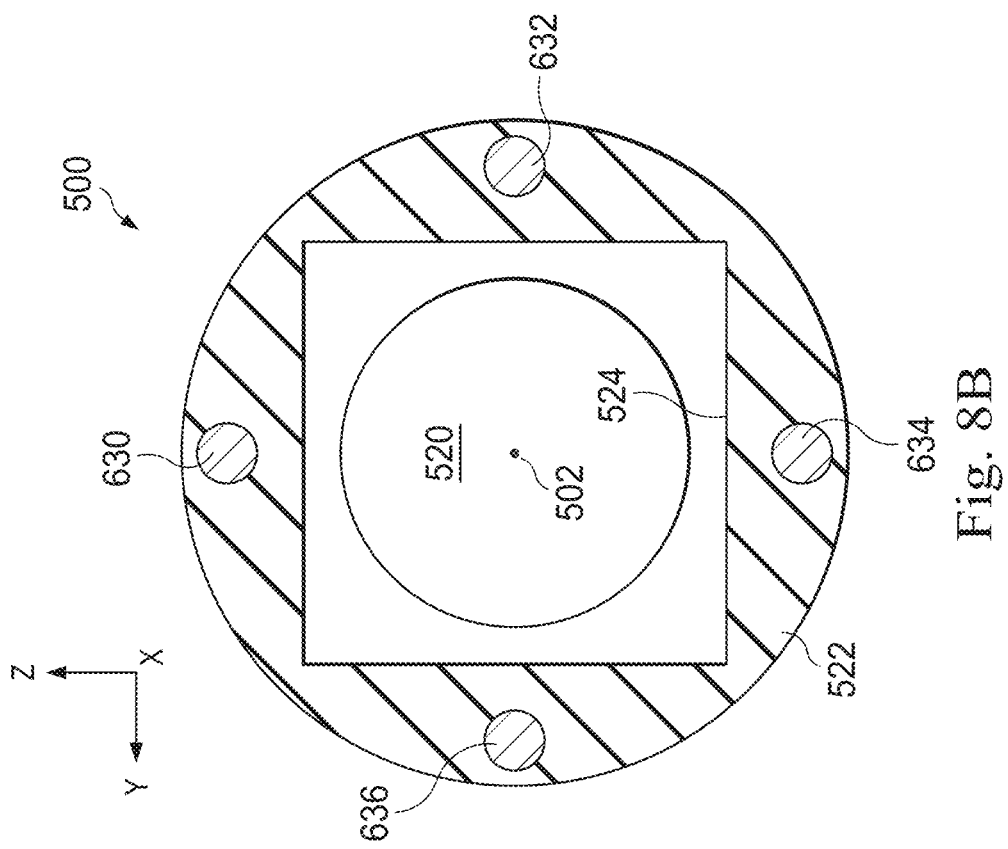
FIG. 8B is a simplified cross-sectional end view of the catheter assembly of FIG. 8A according to some embodiments.

Referring now to FIGS. 8B-8C, a simplified cross-sectional view of the distal portion 518 of the catheter assembly 500 of FIG. 8A is shown. FIG. 8B shows a cross-section of a proximal portion of the tool 520 that has a circular cross-section and the lumen 524 of the catheter 522 has a square cross-section. FIG. 8C shows a cross-section of the catheter assembly 500 at the distal portion 550, which shows the distal portion 550 and the lumen 524 with a square cross-section. The cross-sectional views are viewed in the direction of the viewable region 540 (i.e. toward the distal end 516 of the catheter 522). FIG. 8D shows a tool 520 rotationally aligned with the catheter 522. The angular position 612 of the tool 520 is aligned with the angular position 610 of the catheter 522. The arrow 620 again indicates the top-middle position of the imaging sensor 510 relative to the central axis 502. FIG. 8E shows the tool 520 offset from the catheter 522 by a rotational offset A1. The angular rotation 622 has rotated the distal portion 550 relative to the catheter 522 by a rotational offset A1.

Because the square cross-section of the distal portion 550 is being inserted into a matching (however, slightly larger) square cross-section of the lumen 524 of the catheter 522, there are four rotational offset values that are possible, i.e. 0 (zero), 90, 180, and 270 degrees. A first quadrant Q1 of the tool 520 can be defined as the 0 (zero) degree rotational offset. A second quadrant Q2 of the tool 520 can be defined as the 90 degree rotational offset. A third quadrant Q3 of the tool 520 can be defined as the 180 degree rotational offset. A fourth quadrant Q4 of the tool 520 can be defined as the 270 degree rotational offset. The four quadrants can be seen as being divided by lines 614 and 616 as seen in FIGS. 8D and 8E, and can be seen as being quadrants of images captured by the tool 520. Therefore, referring to a quadrant in an image also refers to the same quadrant of the tool 520. The rotational arrow 622 indicates that the tool 520 was rotated 90 degrees relative to the catheter 522 when it was inserted into the catheter 522. The catheter 522 can include the viewable feature 470, that is viewable by an imaging sensor 510 (not shown) of the tool 520. As the tool 520 is inserted into the catheter 522, captured images from the imaging sensor 510 can indicate which quadrant Q1-Q4 of the captured images that the viewable feature 470 appears in, and the indicated quadrant can be used to determine the rotational offset. The removal of the rotational offset A1 can be performed as described above to produce modified images that are rotationally aligned with the catheter 522.

Figure 8F:
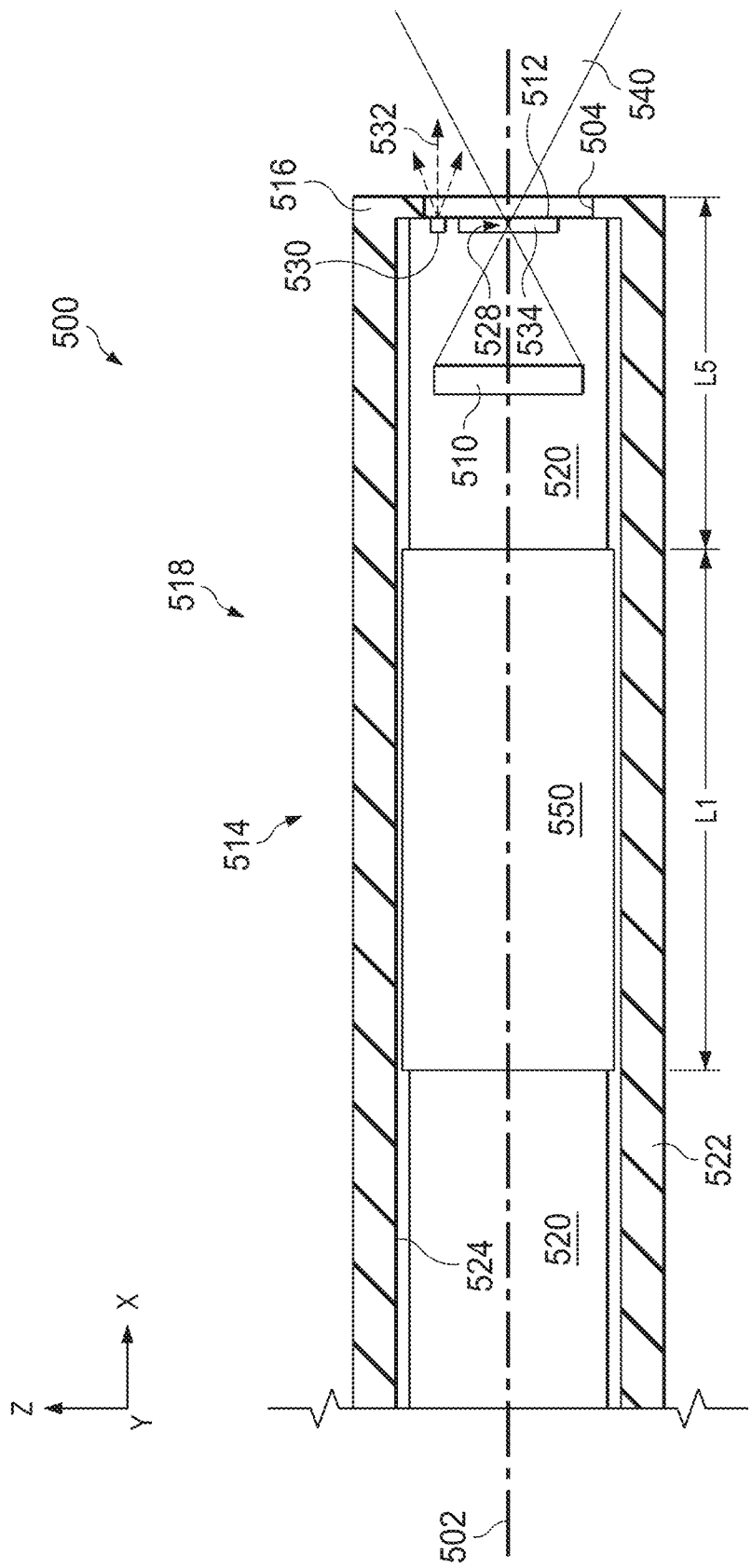
FIG. 8F is a simplified partial cross-sectional view of a distal portion of a catheter assembly with distal portion of a tool having a square cross-section according to some embodiments.
Figure 9A:
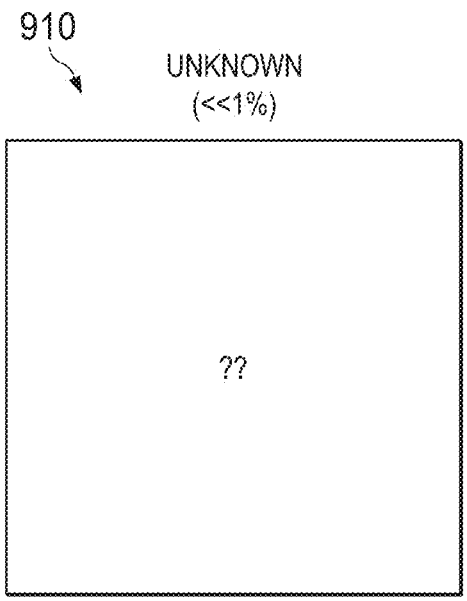
FIGS. 9A-9H are simplified representative images captured by an imaging sensor at various stages of installation in a catheter according to some embodiments.
Figure 9B:
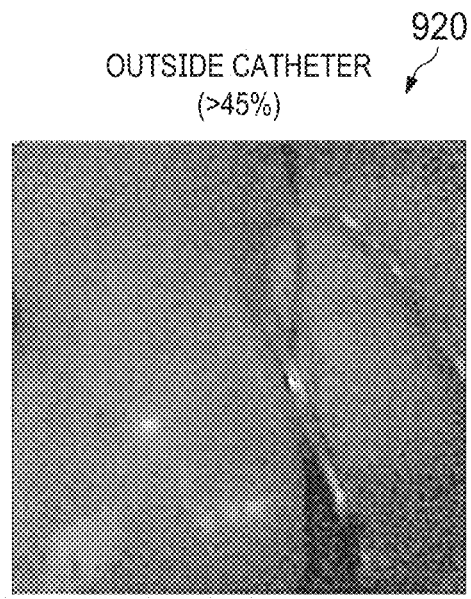
Figure 9C:
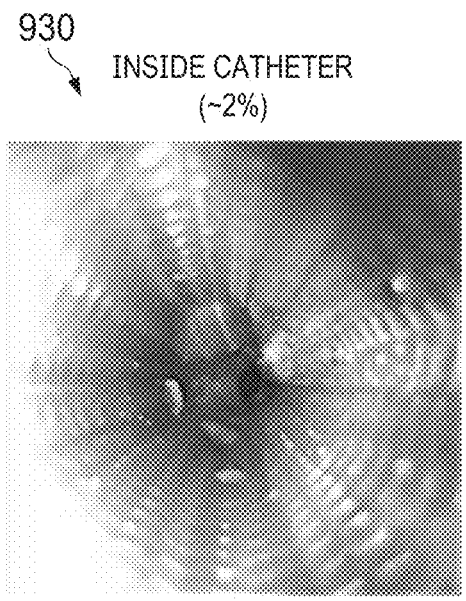
Figure 9D:
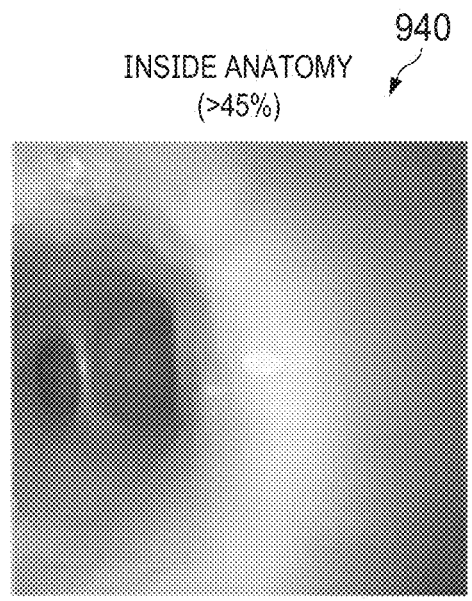
Figure 9E:
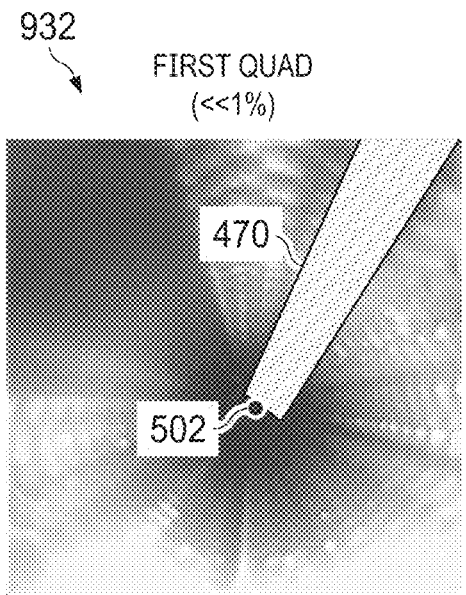
Figure 9F:
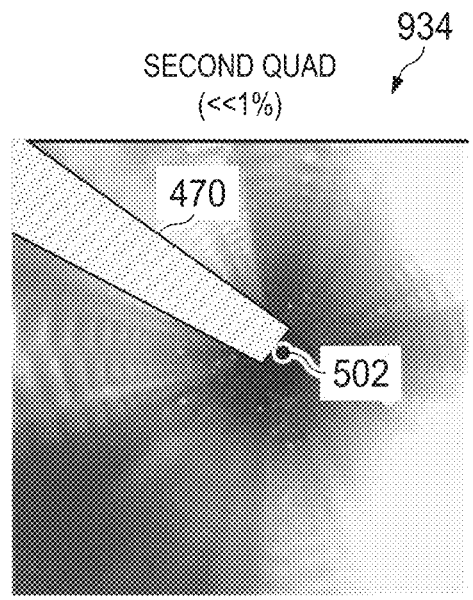
Figure 9G:
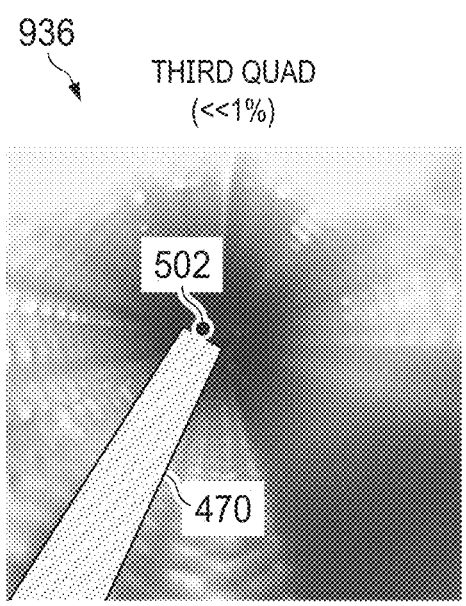
Figure 9H:
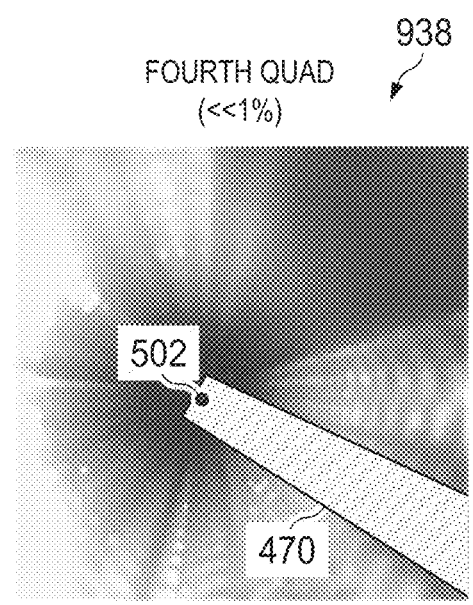

Referring now to FIG. 8F, a simplified partial cross-sectional view of the distal portion 518 of the catheter assembly 500 is shown. This catheter assembly 500 is similar to the catheter assembly in FIG. 8A, except that the distal portion 550 of the tool 520 is spaced away from the distal end of the catheter assembly by a distance L5 and positioned between two other portions of the tool 520 that have a circular cross-section. The distance L5 can range between 50 mm and 200 mm. The distance L5 can be, for example, 50 mm, 60 mm, 70 mm, 80 mm, 90 mm, 100 mm, or 200 mm. The square cross-section of the distal portion 550 matches the square cross-section of the lumen 524 of the catheter 522. The square cross-sections of the distal portion 550 and the lumen 524 do not require an additional key system to prevent rotation of the tool 520 relative to the catheter 522, when the distal portion 550 is inserted into the matching square cross-section of the lumen 524. Some rotation may occur due to clearances between the tool 520 and the catheter 522, but this is minor, and even this minor relative rotation can be compensated for by using the principles of this disclosure. The image sensor 510 can capture pictures from within the catheter 522 when the tool 520 is being installed in the catheter 522, since it takes the length L5 before the square cross-sections of the tool 520 and the catheter 522 engage each other. For this reason, a viewable feature (such as a longitudinal marking) may not be included in a proximal end portion of the catheter 522 to prevent the user from thinking that the portion 550 has engaged the lumen 524 of the catheter 522.

Referring now to FIGS. 9A-9H, the tool 520 with the imaging sensor 510 can capture images 910-940 during the insertion process as the tool 520 is being inserted into the catheter 522 of the catheter assembly 500. The catheter assembly 500 can be similar to the one shown in FIGS. 8A-8E, with the square cross-sections, or similar to the one shown in FIGS. 7A-7E with the circular cross-sections. The principles of this disclosure are equally applicable to either configuration of the catheter assembly 500. Some of the captured images, such as images 910, may be unknown, which means that the image taken has minimal discernible attributes that prevents classifying the image. Images 910 may account for a very small percentage of the captured images. Some of the captured images, such as images 920, can be identified as being outside the catheter 522, such as prior to insertion of the tool 520 into the catheter or just after removal of the tool 520 from the catheter. Images 920 may account for a large percentage of the captured images. Some of the captured images, such as images 930, can be identified as being inside the catheter 522, such as during insertion of the tool 520 into the catheter. Images 930 can account for a small percentage of the captured images. Some of the captured images, such as images 940, can be identified as being outside the catheter 522 and inside the anatomy of a patient. Images 940 may account for a large percentage of the captured images.

The images (e.g., image 930) captured inside the catheter 522 can be one or more of the types of images 932, 934, 936, 938 shown in FIGS. 9E-9H. However, images 932, 934, 936, 938 each generally represent much less than 1% of the total number of images (910-940) collected by the tool 520 during a procedure, due to the relatively small amount of time the imaging sensor 510 of the tool 520 is positioned within the catheter 522. When the tool 520 and the lumen 524 of the catheter 522 have complementary square cross-sections, the tool 520 can be inserted into the catheter 522 in one of four possible rotational orientations defined as quadrants Q1-Q4 (such as shown in FIGS. 8D, 8E). Each one of the images 932, 934, 936, 938 can be seen as indicating one of the quadrants Q1-Q4 by the rotational position of a viewable feature in the images. The viewable feature can be in the form of the longitudinal marking 470 as seen in images 932, 934, 936, 938. Images of all quadrants Q1-Q4 can be collected when the tool 520 is being inserted into the catheter 522, because, in some embodiments, the square cross-section of the lumen 524 may not be extended to a proximal end of catheter 522, with the proximal end possibly being a circular cross-section. The circular cross-section of the proximal end of the lumen can assist in insertion of the tool 520 into the catheter 522, with the square cross-sectional lumen being engaged by the tool 520 past the circular cross-sectional portion. However, it is not required that the proximal end of the lumen 524 be a circular cross-section. For example, in some embodiments the entire lumen 524 can be a square cross-section. Thus, the entire lumen 524 can have the same shape or alternatively, different portions of the lumen 524 can have different shape.

When the captured images 930 (i.e., inside the catheter) include all quadrants, determining the orientation of the tool 520 within the lumen 524 may be difficult due to the lack of sufficient information to make that determination. To increase the information needed to determine the orientation of the tool 520, the amount of images 930 captured while the imaging sensor 510 is positioned within the catheter 522 can be increased. When the square cross-sections of the tool 520 and the lumen 524 is engaged for the sufficient amount of the time the tool 520 is within the catheter 522, additional images can be captured within the lumen 524 of the catheter 522 resulting in a greater percentage of one of the images 932, 934, 936, 938 being captured in the images 930. The image between the images 932, 934, 936, 938 with the highest percentage of the images 930 may show the longitudinal marking 470 in a particular quadrant Q1-Q4, thereby indicating in which quadrant Q1-Q4 the tool 520 is oriented. Based on the quadrant Q1-Q4 indicated by the image between the images 932, 934, 936, 938 being the highest percentage of the images 930, the orientation of the tool 520 can be determined.

Determining the orientation of the tool 520 in the catheter 522 can be similarly performed when the cross-section of both the tool 520 and the lumen 524 are circular or any other shape. In the circular cross-section configuration, however, the tool 520 can possibly rotate between 0 and 360 degrees within the catheter 522. As with the square cross-section configuration, a pattern recognition tool may be used to determine a rotational offset A1 by detecting the longitudinal marking 470 in the captured images and determining the relative orientation of the marking 470 to the captured images. Since the rotational orientation of the marking 470 relative to the catheter 522 is known, the rotational orientation of the catheter 522 relative to the captured image can be determined. While the square cross-section configuration determines the orientation of the tool 520 from four choices for rotational orientation, the circular configuration determines the orientation of the tool 520 from any orientation from 0 to 360 degrees. However, the rotational orientation of the catheter 522 relative to the captured images 930 in the circular cross-section configuration can still be determined using the pattern recognition tool to recognize the marking 470 and its position in the captured images. Then the rotational offset A1 can be determined and thereby the rotational orientation of the catheter 522 relative to the captured images 930 also determined. It should be understood that the captured images 930 may be given different weights to indicate their increased or decreased importance in determining the rotational orientation of the catheter 522. For example, those images 930 taken closer to the distal end 516 of the catheter 522 may be weighted higher (thus increased importance) while those images taken closer to the proximal portion of the catheter 522 may be weighted lower (thus decreased importance). Other weighting criteria may also be used.

Regarding the pattern recognition tool, the current disclosure uses an artificial neural network to recognize patterns in the captured images 930 and report the orientation of the pattern (e.g. the longitudinal marking 470) to a control system for analysis. For the artificial neural network to provide quality results the artificial neural network is trained on what to recognize. Known images with known orientations of the marking 470 may be input into the artificial neural network to train the artificial neural network to associate the image with an orientation of the marking 470. Based on the training, the artificial neural network can recognize the similarities between an unknown image and the known images received during the training process and report on the probability that the unknown image has a marking 470 at a particular rotational orientation. The more known images the artificial neural network receives during training, the more accurate and/or efficient the reported results will be.

Figure 10:
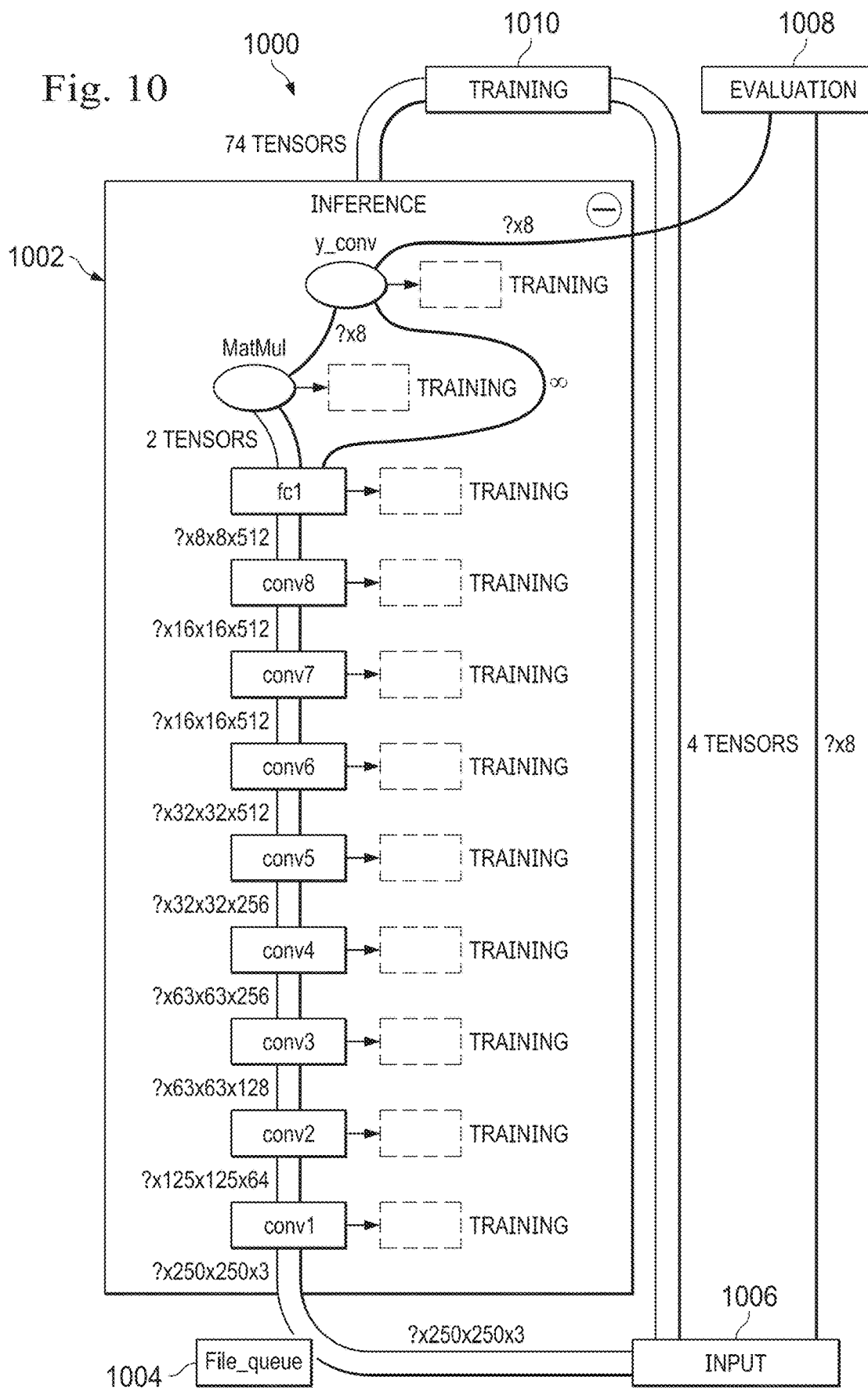
FIG. 10 is a representative functional block diagram of a convolution deep neural network according to some embodiments.

Referring now to FIG. 10, a representative functional block diagram of an artificial neural network 1000 is shown. In this embodiment, the artificial neural network may include a deep convolutional neural network (DCNN) operating within the control system 112 to perform the image recognition function for determining the angular position of the longitudinal marking 470. The artificial neural network 1000 can include multiple convolution layers with each layer including a convolution filter kernel. The artificial neural network 1000 can include convolution layers 1002 (CONV1-CONV8) that can each include a 3×3 convolution filter kernel. In these layers 1002, the 3×3 filter kernels are applied to the images thereby performing a convolution on the images. A nonlinear activation function can follow performing the convolution function. The convolution layers 1002 can be connected to a file queue 1004 that can store the input images received at the input 1006. The evaluation function can determine the quality metric for each of the convolved images and determine a confidence factor related to each of the convolved images. The training module 1010 is used to supply inputs to each of the 3×3 convolution filter kernels (CONV1-CONV8) and other functions of the layers 1002. This training module 1010 is used to train the neural network 1000.

The artificial neural network 1000 is trained to detect specific attributes in the input images and generate corresponding outputs based on valid detections made in the input images. To train the artificial neural network 1000 to recognize the specific attributes in given images, a plurality of training images are provided as input to the neural network, where the training images include the specific attributes (such as the longitudinal marking 470) to be detected. As stated above, the more training images provided to the neural network, the better the neural network's efficiency can be, at least to a maximum realizable efficiency. However, as can be seen from the captured images 910-940 in FIG. 9, the percentage of images 930 within the captured images 910-940 is very small. Moreover, the percentage of each of images 932, 934, 936, 938 within the captured images 910-940 can be even smaller. The low percentages of images 930 and images 932, 934, 936, 938 can be attributed to the limited amount of time it takes to install the tool 520 in the catheter 552, especially if the inserting is performed as a part of a medical procedure, when downtime of the teleoperational system 400 will desirably be minimized. To build up the number of training images, a number of tool insertions may be performed.

In some layers of the artificial neural network (ANN) 1000, pooling can be also applied, typically by downsampling to a max value over a small kernel. There can be one or more fully connected layers at the end, which are connected to the output (evaluation module 1008). In training, the training images can be read into the network 1000 at input 1006, the output from the neural network 1000 is compared to a ground truth image at an evaluation module 1008 to determine the error rate of the neural network 1000. The ground truth image may be established by the training images that are labeled to be the standard by which to compare captured images 930. A ground truth image in this case may be a training image that has the marking 470 at an orientation in the training image that indicates that the catheter 522 is rotationally aligned with the tool 520. When captured images are compared to the ground truth images used in training, a difference between the position of the marking 470 in the ground truth image and the position of the marking 470 of the captured image may be determined. Adjustments to the neural network weight parameters are performed automatically by software used to implement the neural network 1000. The training images can be processed by the network multiple times as the neural network 1000 computes output, calculates errors, and adjusts weights, until the percent of correctly classified images is sufficiently high (e.g. >90%). Once the training is complete, the final weights used in training the neural network are recorded so the network can be used to classify new images during an actual procedure.

As described below, data replication and perturbations may be used to generate a quantity of training images to train the neural network 1000 to achieve greater than 90% efficiency, or greater than 95% efficiency, or greater than 97% efficiency, where efficiency is the measure of the amount of times the neural network 1000 provides an accurate result when requested compared to the total number of times a result is requested. The training images should provide a wide range of image attributes to allow the neural network to produce the correct results with actual operational images that may not exactly match the initial small set of captured images 932, 934, 936, 938.

The images 932, 934, 936, 938 can be replicated and manipulated to produce thousands of training images for the neural network 1000 with varied attributes to provide quality training. For the catheter assemblies of FIGS. 8A and 8F, the images can be restricted to replicating images for each of the four quadrants Q1-Q4, but not necessarily for other angular offsets. However, it should be understood that the principles of this disclosure are not limited to the four quadrants Q1-Q4. The image replication can produce thousands or more of training images for each quadrant by replicating one or more of the images 932, 934, 936, 938 collected during an insertion of the tool 520. Various ones of the replicated images can also be rotated to produce training images with the longitudinal marking 470 in each of the quadrants Q1-Q4.

Figure 11A:
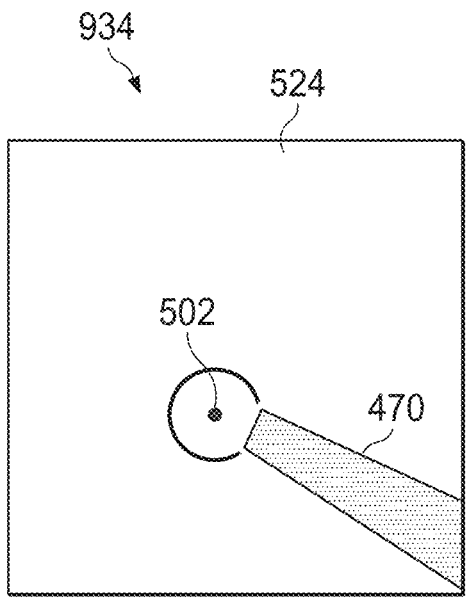
FIGS. 11A-11L are simplified representative training images replicated and manipulated from original images captured during installation of an imaging sensor into a catheter according to some embodiments.
Figure 11B:
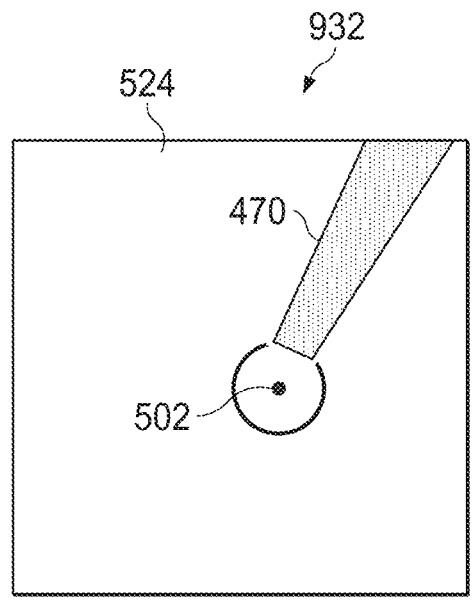
Figure 11C:
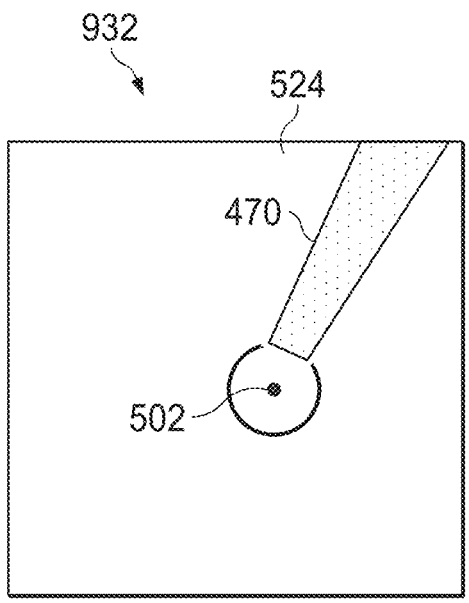
Figure 11D:
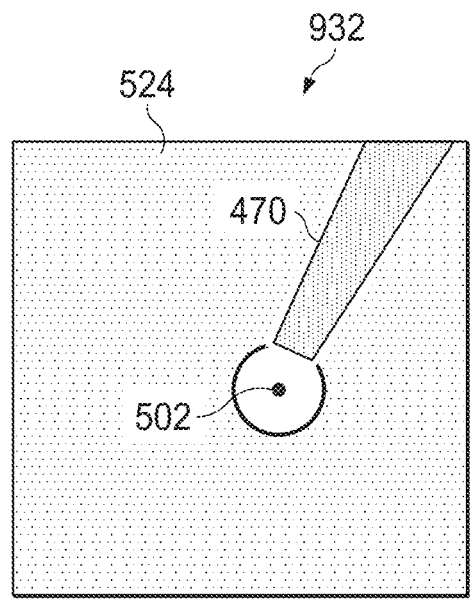
Figure 11E:
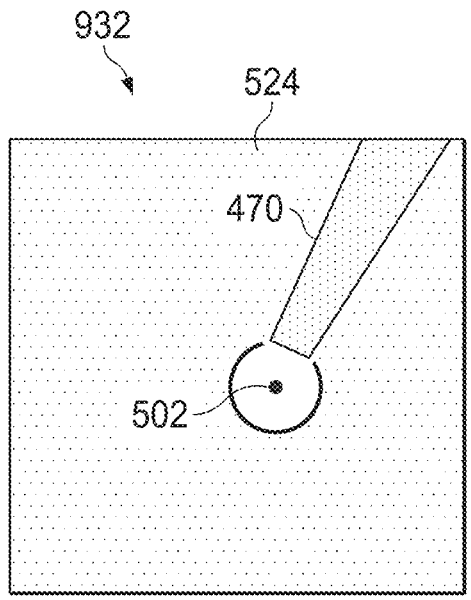
Figure 11F:
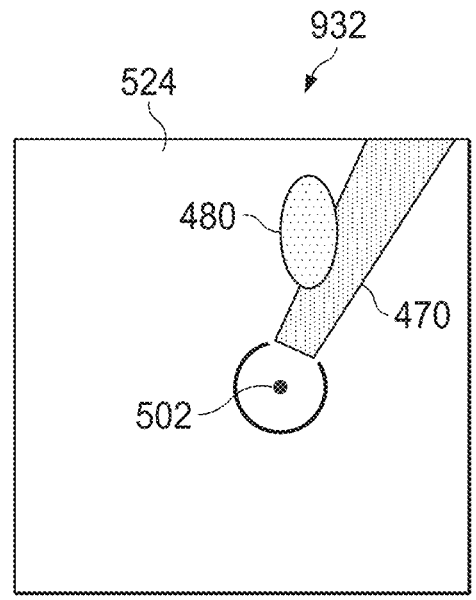
Figure 11G:
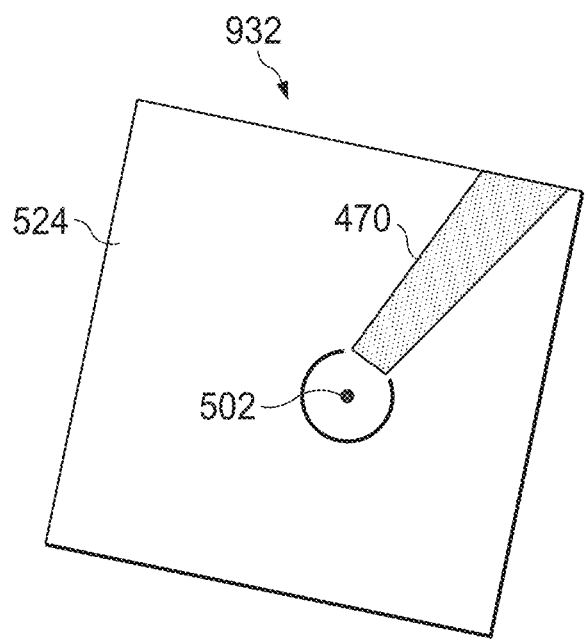
Figure 11H:
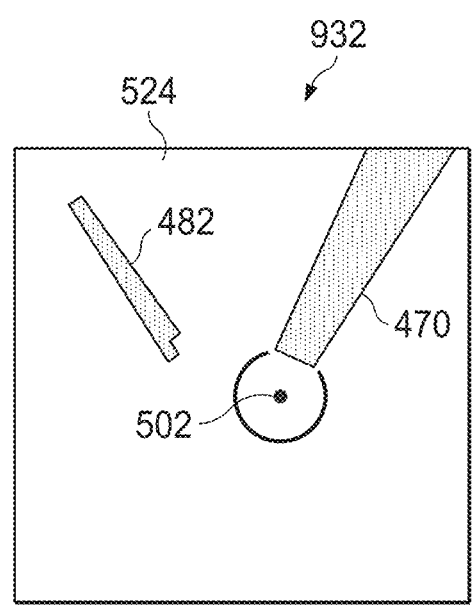
Figure 11I:
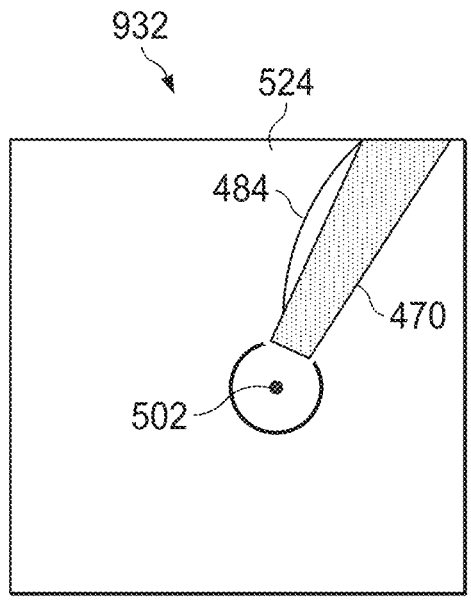
Figure 11J:
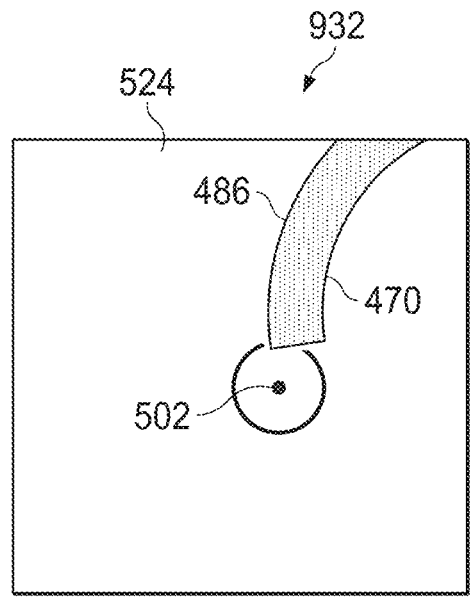
Figure 11K:
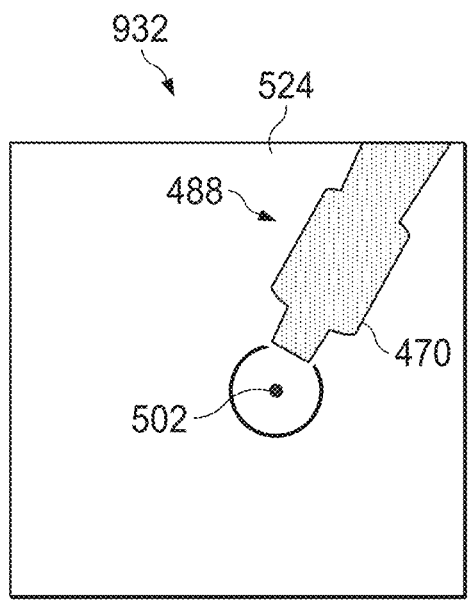
Figure 11L:
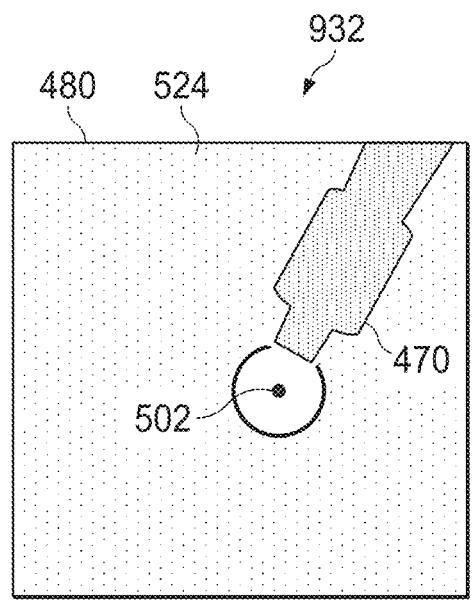

The replicated images can also be manipulated to produce a large number of training images with varied attributes. For example, referring to FIGS. 11A-11L, one training image for quadrant Q1 can be created by copying an image 934 for quadrant Q2, rotating the image clockwise by 90 degrees, and replicating the rotated image many times (e.g. FIGS. 11B-11L). Various ones of the replicated images can be modified by changing the color (e.g. applying a color variance) of the longitudinal marking 470 (FIG. 11C), changing the color of the lumen 524 (FIG. 11D), changing the contrast between the marking 470 and the lumen 524 (FIG. 11E), changing the brightness of the image (FIG. 11D), rotating the image slightly more or less than 90 degrees (FIG. 11G), adding other features that may represent objects that are desirably ignored when processing the image (e.g. liquid droplets 480 in the lumen (FIG. 11F), liquid droplets 480 obscuring the marking 470 (FIG. 11F), other longitudinal markings 482 that are not the marking 470 (FIG. 11H)), changing the shape of the marking 470 along its length (e.g. widen or narrow 484 portions of the marking 470 (FIG. 11I, 11K, 11L), slightly curve the marking 486 (FIG. 11J), or combinations thereof), changing the image to emulate significant catheter distortion 488 around a tight bend (FIG. 11L), or combinations thereof.

The neural network 1000 can be used to determine the rotational offset A1 of images 930 captured during a procedure. Additionally, the neural network 1000 can be used to determine the location of the tool 520. By training the neural network 1000 with all images 920-940, including all the replicated images 930, the neural network 1000 can determine the location by identifying the type of image that has been captured by the tool 520. For example, if the tool 520 (i.e. the imaging sensor 510) captures an image like image 920, then the neural network 1000 can report that the tool 520 is not yet installed in the catheter 522, since the images indicated the tool 520 is outside the catheter 522. If the tool 520 captures an image like image 930, 932, 934, 936, 938, then the neural network 1000 can report that the tool 520 is at least partially installed in the catheter 522 but not extended into the patient anatomy. If the tool 520 captures an image like image 940, then the neural network 1000 can report that the tool 520 is outside of the catheter 522 and extended into the patient anatomy. Additionally, if any images like the images 932, 934, 936, 938 are captured, the neural network 1000 can report that the tool 520 is at least partially installed in the catheter 522, and to which quadrant Q1-Q4 the tool 520 is oriented.

Figure 12A:
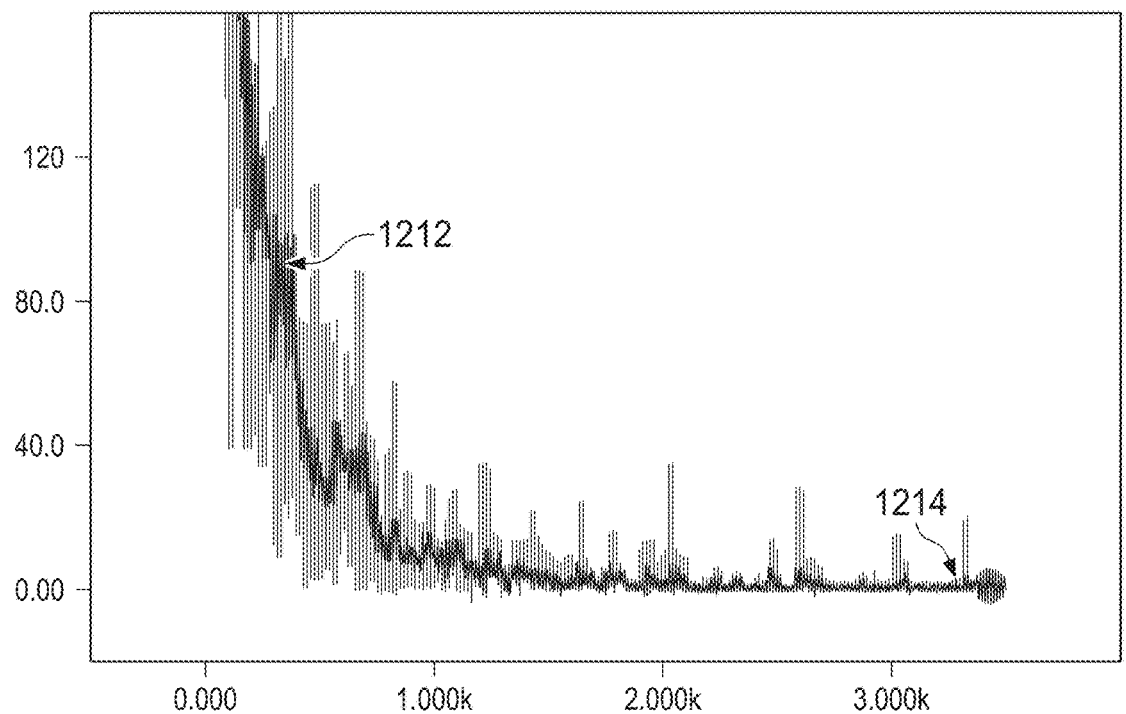
FIGS. 12A-12B are representative plots of cross entropy and training accuracy of a neural network for image recognition according to some embodiments.
Figure 12B:
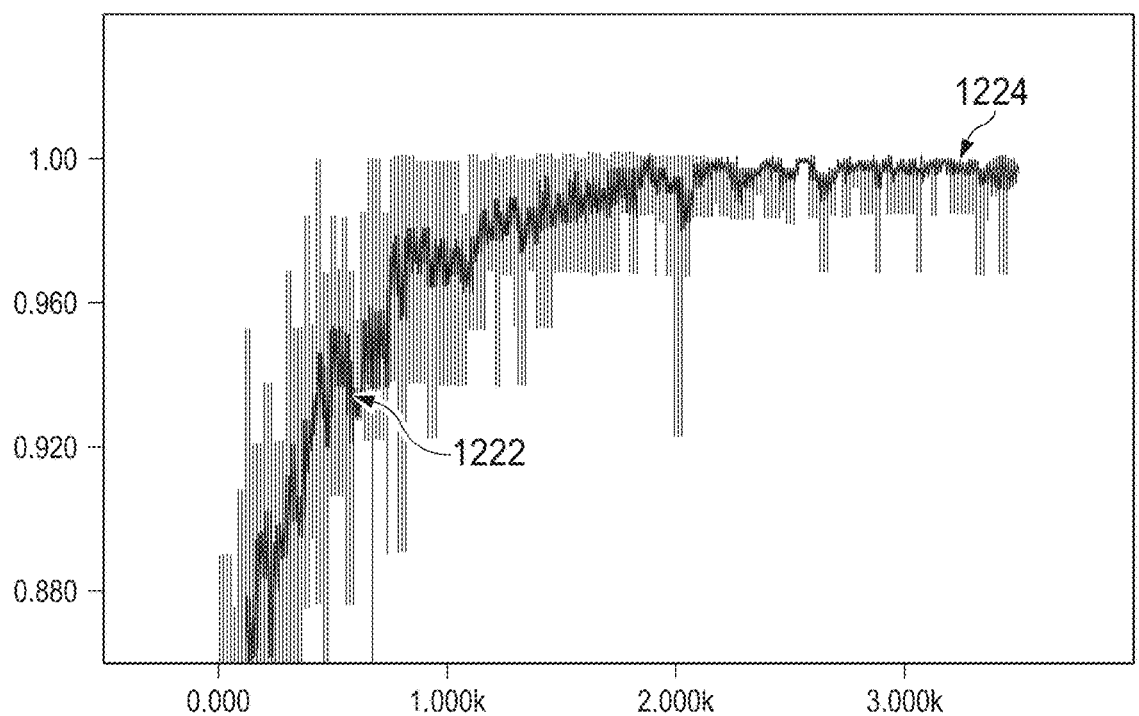

Referring now to FIGS. 12A, 12B, plots 1210 and 1220 are shown. The plot 1210 shows a cross entropy of the neural network 1000 as the amount of training images processed by the neural network 1000 increases. The lower the cross entropy, the better the neural network 1000 provides accurate results. Point 1212 of plot 1210 is calculated with less than a thousand training images processed. This point 1212 is significantly higher than the point 1214 of the plot 1210, which is calculated with over 3000 training images processed. Similarly, the plot 1220 shows that performance of the neural network 1000 improves with greater amounts of training images being processed. Plot 1220 shows a training accuracy of the neural network 1000 as the amount of training images processed by the neural network 1000 increases. Point 1222 of plot 1220 is calculated with less than a thousand training images processed. This point 1222 is significantly lower than the point 1214 of the plot 1210, which is calculated with over 3000 training images processed. At some point, adding more training images may not significantly improve the performance of the neural network 1000, as seen by the minimal change in the cross entropy and the training accuracy values between 2000 to 3000 training images.

Figure 13A:
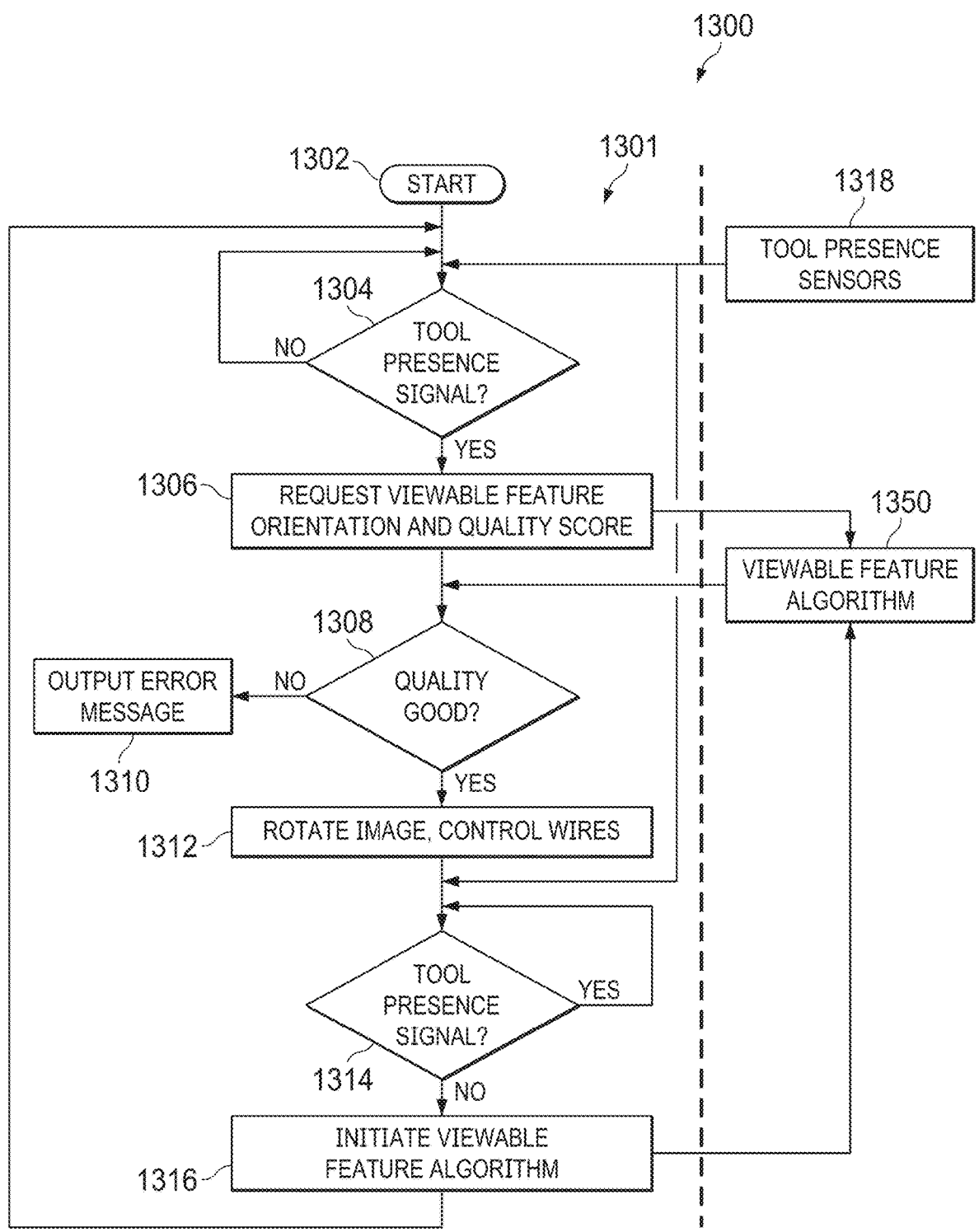
FIG. 13A is a representative flow chart for controlling collection and adjustments of images during a procedure according to some embodiments.
Figure 13B:
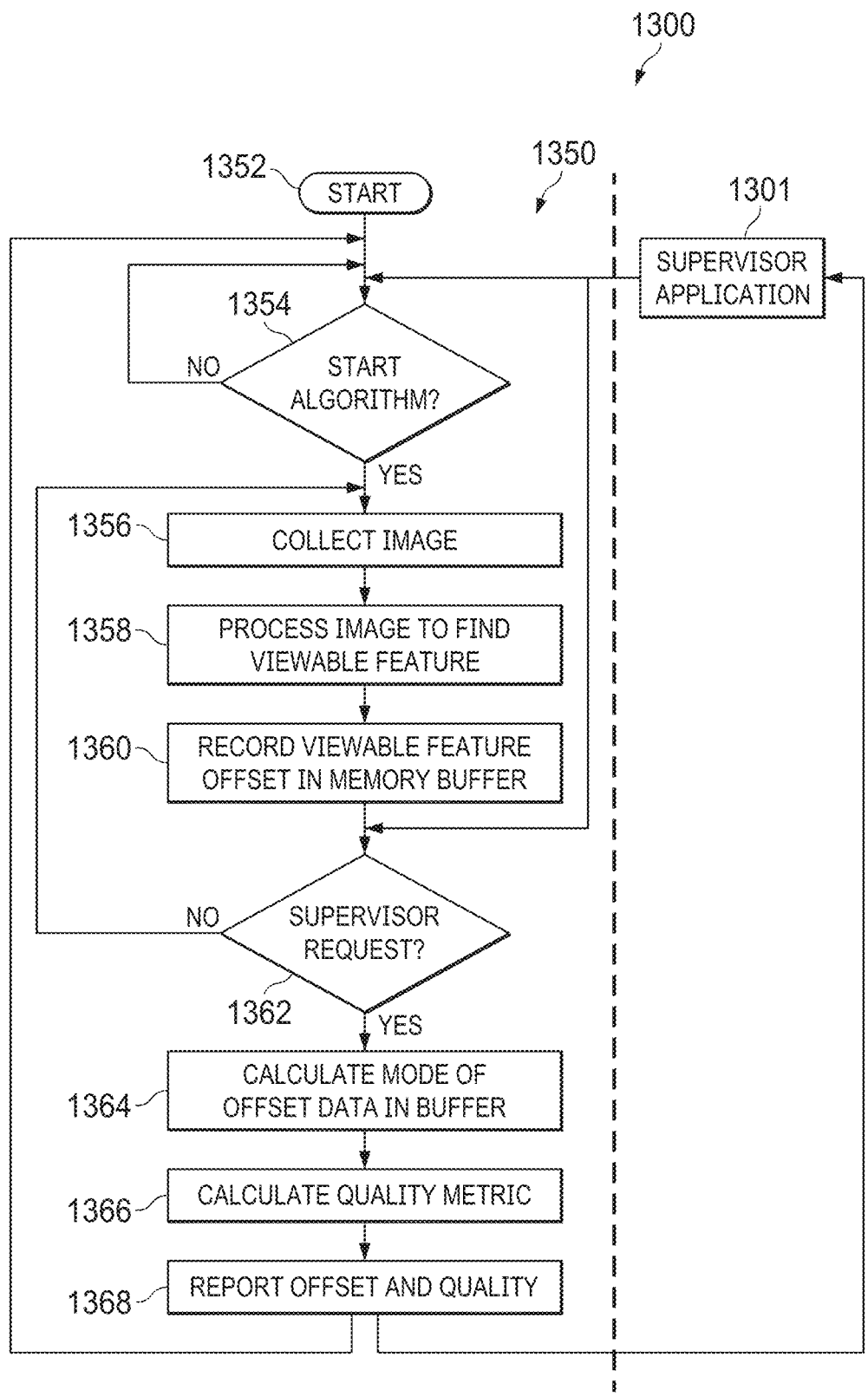
FIG. 13B is a representative flow chart for controlling when rotational offsets of images are collected during a procedure and reported to the control system according to some embodiments.
Figure 13C:
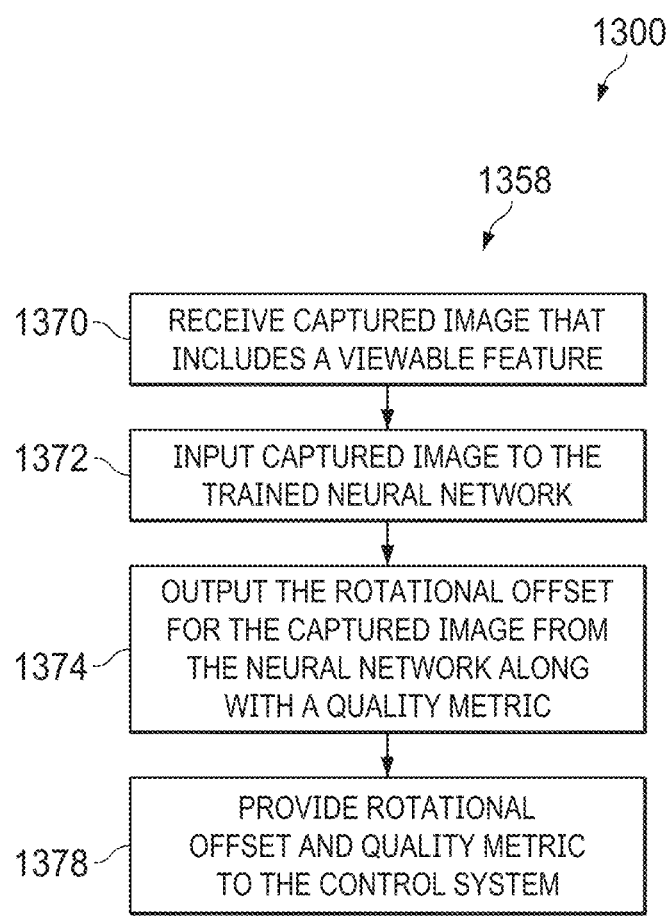
FIG. 13C is a representative flow chart for detecting a viewable feature in a captured image and determining a rotational offset of the viewable feature according to some embodiments.

A method 1300 for controlling collection and adjustments of images during a procedure is illustrated in FIGS. 13A-13C as a set of operations or processes 1302 through 1378. Not all of the illustrated processes 1302 through 1376 may be performed in all embodiments of method 1300. Additionally, one or more processes that are not expressly illustrated in FIG. 13A-13C may be included before, after, in between, or as part of the processes 1302 through 1378. In some embodiments, one or more of the processes may be implemented, at least in part, in the form of executable code stored on non-transitory, tangible, machine-readable media that when run by one or more processors (e.g., the processors of control system 112) may cause the one or more processors to perform one or more of the processes.

Referring now to FIGS. 13A-13C, representative flow charts for the method 1300 of controlling the collection of images during a procedure, determining a rotational offset of an imaging sensor, and correcting captured images by removing the rotational offset prior to displaying the captured images to a user are illustrated. FIG. 13A is a representative flow chart of a supervisor process 1301 that can control the collection and correction of images during a procedure. The process 1301 can initiate and control the process 1350 (see FIG. 13B) to determine a rotational offset of the tool 520 in a catheter 522 and receive the rotational offset and quality metrics of collected and calculated data. The process 1350 can initiate the process 1358 (see FIG. 13C) to analyze a captured image to determine the rotational offset. The following paragraphs describe these processes in more detail.

The supervisor process 1301 begins when an indication (e.g., a user input) is received to start the process at operation 1302. Operation 1304 determines whether a tool 520 is present in the catheter 522 based on detecting a tool presence signal, for example. A tool presence signal can be detected by operation 1318, which monitors tool presence sensors to determine whether the tool 520 is partially or fully inserted into the catheter 522 based on insertion signatures detected by one or more target readers (or sensors) or not inserted at all. When it is determined that the tool 520 is partially inserted, the supervisor process 1301 can proceed to other operations to detect a viewable feature, such as a longitudinal marking within the lumen 524 of the catheter 522 to determine a rotational offset A1 of the tool 520 in the catheter 522. However, when it is determined that the tool 520 is fully inserted in the catheter 522, the longitudinal marking within the lumen 524 may not be viewable. Therefore, the supervisor process 1301 can proceed to other operations to detect other viewable features than the longitudinal marking (e.g. other viewable features described in this disclosure) that can be used to determine the rotational offset A1 of the tool 520 in the catheter 522. These other viewable features can be portions of the catheter 522 extended beyond the distal end of the tool 520 and/or objects outside the catheter 522. When it is determined that the tool 520 is not inserted into the catheter 522, then the supervisor process 1901 can hold in operation 1904 waiting on a positive indication that the tool is at least partially inserted into the catheter. When the positive indication is received, the supervisor process 1301 can proceed to operation 1306, which can request an orientation (or angular position) of a viewable feature 470 captured in an image, and a quality scoring of the collected and calculated information (such as the angular position of the viewable feature). The process 1350 collects images and determines the rotational offset A1 of a viewable feature 470 in at least one of the collected images, as well as a quality metric that can provide a weighting as to the confidence in the information provided back to the supervisor process 1301. At process 1308, the supervisor process 1301 determines the quality of the information from the operation 1350. If the supervisor process 1301 determines that the quality of the information from the operation 1350 is below a threshold level, then operation 1310 can output an error message to the control system 112, which can alert the user and/or log the error message for later review.

If the quality of the information from the operation 1350 is determined at process 1308 to be above a threshold level, then operation 1312 can use the information to rotate operational images to remove the rotational offset A1 and/or adjust the manipulations of the control cables 630, 632, 634, 636 as described in more detail above (e.g. through the use of manipulation instructions). Operation 1312 can continue while operation 1314 continues to monitor the tool presence signal supplied by the operation 1318. As long as the tool presence signal remains active, indicating no change in the tool location in the catheter, then the operation 1312 can continue. When the tool presence signal is no longer active (i.e. if the tool 520 has been moved from fully inserted, or removed all together from the catheter 522), then the process 1301 may proceed to operation 1316 that can request initiation of the viewable feature process 1350, again. This may be desirable if the tool 520 remains partially inserted in the catheter 522, and the viewable feature process 1350 can again determine an orientation of the tool 520 in the catheter by detecting the viewable feature, which in this case, can be a longitudinal marking 470. The process 1301 can also proceed from operation 1316 to operation 1302 to restart the process and proceed to operation 1304 to again wait on a positive tool presence indicator before continuing with operations in the process 1301.

Referring to FIG. 13B, the process 1350 for controlling when rotational offsets of images are collected during a procedure and reported to the control system starts at operation 1352 and proceeds to operation 1354 which can wait on an indication from the supervisor process 1301 to start the algorithm for the process 1350. When the rotational offset of the tool 520 within a catheter 522 is desired, the supervisor process 1301 can send a positive signal to the process 1350 to proceed to the next operation. In operation 1356, an image (or images) can be captured by the imaging sensor, where the captured image(s) can include the viewable feature 470. In operation 1358, the image(s) are processed to identify the viewable feature 470 and its rotational offset A1 relative to the catheter 522. The image processing at operation 1358 may pass the collected images to the neural network 1000 and have the neural network 1000 output the predicted rotational offset A1 as well as a quality metric that can assign a confidence percentage to the results of the neural network 1000.

In operation 1360, the information determined in operation 1358 can be stored in a memory buffer for later analysis and calculations. Operation 1362 checks to determine whether the supervisor process 1301 has requested data. If a data request from the supervisor process 1301 is not indicated, the process 1350 continues to repeat processes 1356, 1358, 1360 and 1362 until a data request is indicated. Since process 1350 can be started while the tool 520 is being installed in the catheter 522, the memory buffer will store multiple images captured within the catheter 522.

A data request may occur when a positive tool presence signal is received by the supervisor process 1301. A positive tool presence signal can indicate that multiple images have already been stored in the memory buffer since images were collected during the installation of the tool 520. Responsive to a data request from the supervisor process 1301, the process 1350 proceeds to operation 1364 to analyze the data in the memory buffer, calculate a rotational offset for each image, and calculate a statistical mode across the multiple images that best describe the rotational position of the tool 520 within the catheter 522. Operation 1366 can calculate a quality metric to indicate the confidence of the calculated rotational offset of the tool 520. The quality metric can include a determination for each processed image as to the confidence that the image contained the viewable feature (e.g. the longitudinal marking) and the confidence of the angular position of the viewable feature in the image. Operation 1368 reports the rotational offset and quality metric to the supervisor process 1301, and returns the process 1350 back to operation 1354 to again wait for a start algorithm indication from the supervisor process 1301.

In general, the supervisor process 1301 may provide the signal or indication to start the algorithm for the process 1350 when the tool presence indication is negative, but not request data from the process 1362. When the tool presence indication is positive, the start algorithm indication can be negative, with the data request indication being positive, causing the calculated data to be transmitted to the supervisor process 1301. The supervisor process 1301 can be directed at the system that detects a rotational offset for a tool 520 in a catheter as the tool is being inserted in the catheter 522. However, the process 1301 can also support the embodiments where the tool 520 is fully installed in the catheter 522 and images captured by the imaging sensor 510 of a viewable region which includes a viewable feature 470. The start algorithm indications and data request indications can be supplied to the process 1350 at times other than those mentioned above and can cause multiple images to be collected when the tool 520 is fully installed, and data requests to be indicated at various times during the procedure, as long as the tool 520 remains fully installed in the catheter 522.

Referring now to FIG. 13C, operation 1358 that processes the images to identify the viewable feature 470 and its rotational offset A1 relative to the catheter 522 can include multiple operations as shown. Operation 1370 can receive captured images, where the captured images can include a viewable feature 470. Operation 1372 can isolate the viewable feature 470 in the captured image. For example, the captured images can be modified to remove the background, and leave the subset of pixels associated with the viewable feature in the images. Removing the background from the images can be done by comparing a baseline image to a captured image with a viewable feature 470. The differences between the two images should be largely due to the viewable feature 470. Therefore, removing the subset of pixels that are basically the same between the two images, will leave the viewable feature still viewable in the modified image. It should be understood, that removing the subset of pixels may not necessarily mean that the pixels are deleted from the image, but merely changed to a value that renders the pixels in the subset to be Red=Blue=Green which is "0 (zero)."

Another way to remove (or set to zero) the pixels associated with a background can include performing a "white balance correction" by identifying a background color and setting the background pixels to a neutral color and leave the contrast of the viewable feature 470. The viewable feature 470 can then be extracted into another image without the background. Once the viewable feature 470 has been isolated in operation 1372, operation 1374 can compare the modified image with the viewable feature 470 to a plurality of model images and an angular position of the viewable feature can be determined based on one or more matches to the model images. Operation 1376 can calculate the rotational offset A1 based on the angular position of the viewable feature 470. Operation 1378 can provide the calculated rotational offset A1 to the process 1358.

One or more elements in the embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Figure 14:
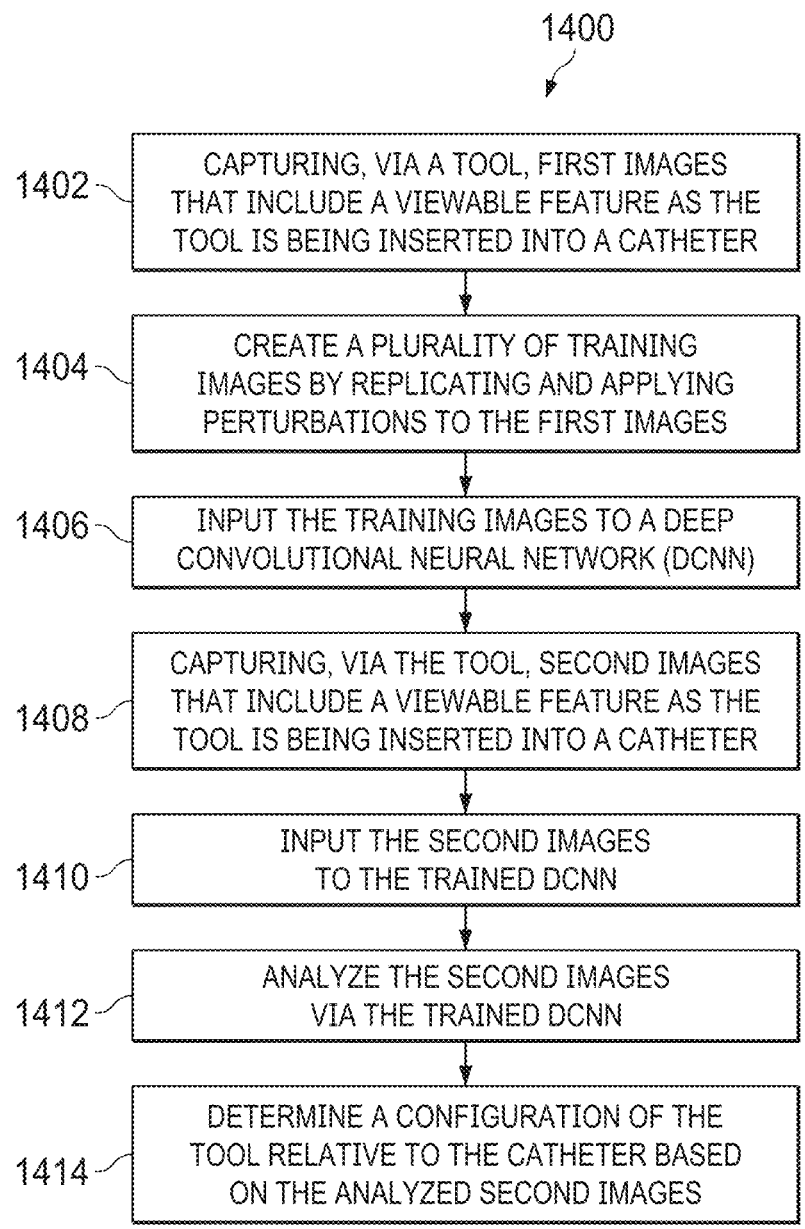
FIG. 14 is a representative flow chart for creating training images with a viewable feature for a neural network, training the neural network with the images, detecting a viewable feature in subsequent captured images, and determining a configuration of a tool in a catheter based on an analysis of the subsequent images by the neural network according to some embodiments.

Referring now to FIG. 14, a representative flow chart 1400 is given for determining a configuration of a tool in a catheter based on an analysis of captured images by a neural network. As described in detail above, it may be desirable to determine a configuration of a tool 520 that has been inserted into a catheter 522. The tool 520 can include an imaging sensor 510 that can capture images as the tool 520 is being aligned with and inserted into a catheter 522. In operation 1402, first images 930 may be captured via the tool 520 as the tool 520 is being inserted into the catheter 522. A viewable feature 470 can be on an inside surface of the catheter 522 and/or outside the catheter 522. The captured first images 930 may include the viewable feature 470 at a particular orientation in the captured first images 930. In operation 1404, these captured first images 930 may be replicated and perturbations applied to create a plurality of training images. In operation 1406, the training images may be input into a deep convolutional neural network (DCNN), thereby training the DCNN to recognize the orientation of the viewable feature 470 within the images. In operation 1408, second images can be captured as the tool 520 is reinserted in the catheter 522 or inserted into another catheter 522. The second images may also contain the viewable feature 470 at some orientation in the second images. In operation 1410, the second images may be input into the trained DCNN, which may analyze the second images in operation 1412. From the analysis of the second images, the DCNN, in operation 1414, may determine a configuration of the tool 520 relative to the catheter 522. The determined configuration of the tool 520 can include a determination that a position of the tool is one of outside the catheter, inside the catheter and not extended into a patient anatomy, and inside the catheter and extended into the patient anatomy. The configuration of the tool 520 can also include a rotational offset between the tool 520 and the catheter 522. With the configuration determined, a procedure utilizing the tool 520 and catheter 522 can proceed to make adjustments based on the determined configuration.

Note that the processes and displays presented may not inherently be related to any particular computer or other apparatus. The required structure for a variety of these systems will appear as elements in the claims. In addition, the embodiments are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A method for determining a position of a tool being received by a catheter, the method comprising:
   capturing first images of the catheter with the tool as the tool is being installed in the catheter;
   inputting the first images into a deep convolutional neural network (DCNN) trained using training images generated by replicating and applying perturbations to second images from one or more second tools captured as the one or more second tools are being installed in one or more second catheters;
   analyzing the first images with the DCNN; and
   determining a configuration of the tool based on the analyzing of the first images.

2. The method of claim 1, wherein the determining the configuration includes determining that a position of the tool is one of outside the catheter, inside the catheter and not extended into a patient anatomy, or inside the catheter and extended into the patient anatomy.

3. The method of claim 1, wherein the determining the configuration includes:
   determining an angular orientation of a feature in the first images; and
   determining a rotational offset of the tool relative to the catheter based on the angular orientation of the feature.

4. The method of claim 3, further comprising:
   rotating the first images by the rotational offset; and
   displaying the rotated first images on a display unit.

5. The method of claim 3, further comprising:
   receiving manipulation instructions for manipulating a set of control cables to articulate a distal portion of the catheter;
   determining adjusted manipulation instructions for manipulating the set of control cables based on the rotational offset; and
   applying the adjusted manipulation instructions to articulate the distal portion of the catheter.

6. The method of claim 3, wherein a distal portion of the tool has a square cross-section and a lumen of the catheter has a complimentary square cross-section, and wherein the rotational offset is selected from a group consisting of 0 (zero), 90, 180, and 270 degrees.

7. The method of claim 3, wherein the tool has a circular cross-section and a lumen of the catheter has a complimentary circular cross-section, and wherein the rotational offset is within a range of 0 to 360 degrees.

8. The method of claim 3, wherein the feature is a longitudinal marking that extends longitudinally along an interior wall of the catheter and wherein the second images used to train the DCNN depict the longitudinal marking.

9. The method of claim 1, further comprising:
   capturing the second images with the one or more second tools as the one or more second tools are being installed in the one or more second catheters;
   generating the training images for the DCNN by replicating the second images and applying perturbations to the replicated second images, wherein applying perturbations to the replicated second images includes applying rotations to the replicated second images; and
   training the DCNN, before capturing the first images, by inputting the training images into the DCNN.

10. The method of claim 1, further comprising:
    capturing the second images with the one or more second tools as the one or more second tools are being installed in the one or more second catheters;
    generating the training images for the DCNN by replicating the second images and applying perturbations to the replicated second images, wherein applying perturbations to the replicated second images includes applying color variances to the replicated second images; and training the DCNN, before capturing the first images, by inputting the training images into the DCNN.

11. A system comprising:
a catheter sized to receive an imaging tool; and
one or more processors configured to:
receive first images of the catheter from the tool as the tool is being inserted in the catheter;
input the first images into a deep convolutional neural network (DCNN) trained using training images generated by replicating and applying perturbations to second images from one or more second tools captured as the one or more second tools are being installed in one or more second catheters;
analyze the first images with the DCNN; and
determine a configuration of the tool based on the analyzing of the first images.

12. The system of claim 11, wherein determining the configuration includes a determination that a position of the tool is one of outside the catheter, inside the catheter and not extended into a patient anatomy, or inside the catheter and extended into the patient anatomy.

13. The system of claim 11, wherein determining the configuration includes:
determination of an angular orientation of a feature in the first images; and
determination of a rotational offset of the tool relative to the catheter based on the angular orientation of the feature.

14. The system of claim 13, wherein the one or more processors are further configured to:
rotate the first images by the rotational offset; and
display the rotated first images on a display unit.

15. The system of claim 13, wherein the one or more processors are further configured to:
receive manipulation instructions for manipulating a set of control cables to articulate a distal portion of the catheter;
determine adjusted manipulation instructions for manipulating the set of control cables based on the rotational offset; and
apply the adjusted manipulation instructions to articulate the distal portion of the catheter.

16. The system of claim 13, wherein a distal portion of the tool has a square cross-section and a lumen of the catheter has a complimentary square cross-section, and wherein the rotational offset is selected from a group consisting of 0 (zero), 90, 180, and 270 degrees.

17. The system of claim 13, wherein the tool has a circular cross-section and a lumen of the catheter has a complimentary circular cross-section, and wherein the rotational offset is within a range of 0 to 360 degrees.

18. The system of claim 13, wherein the feature is a longitudinal marking that extends longitudinally along an interior wall of the catheter and wherein the training images depict the longitudinal marking.

19. The system of claim 11, wherein the one or more processors are further configured to:
receive the second images from the one or more second tools as the one or more second tools are being inserted in the one or more second catheters;
generate the training images for the DCNN by replicating the second images and applying perturbations to the replicated second images, wherein applying perturbations to the replicated second images includes applying rotations to the replicated second images; and
train the DCNN, before capturing the first images, by inputting the training images into the DCNN.

20. The system of claim 11, wherein the one or more processors are further configured to:
receive the second images from the one or more second tools as the one or more second tools are being inserted in the one or more second catheters;
generate the training images for the DCNN by replicating the second images and applying perturbations to the replicated second images, wherein applying perturbations to the replicated second images includes applying color variances to the replicated second images; and
train the DCNN, before capturing the first images, by inputting the training images into the DCNN.

21. The system of claim 11, wherein the one or more second catheters include the catheter and the one or more second tools include the tool.

22. The method of claim 1, wherein the one or more second catheters include the catheter and the one or more second tools include the tool.

* * * * *